United States Patent
Lindsey et al.

(10) Patent No.: US 8,013,149 B2
(45) Date of Patent: ***Sep. 6, 2011

(54) METHODS AND INTERMEDIATES FOR THE SYNTHESIS OF PORPHYRINS

(75) Inventors: Jonathan S. Lindsey, Raleigh, NC (US); Masahiko Taniguchi, Raleigh, NC (US); Arumugham Balakumar, Raleigh, NC (US); Dazhong Fan, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,711

(22) Filed: Jun. 30, 2009

(65) Prior Publication Data

US 2009/0270638 A1    Oct. 29, 2009

Related U.S. Application Data

(62) Division of application No. 11/193,562, filed on Jul. 29, 2005, now Pat. No. 7,582,751.

(51) Int. Cl.
*C07B 47/00* (2006.01)
*C07D 487/22* (2006.01)
(52) U.S. Cl. .................................................. 540/145
(58) Field of Classification Search ............... 540/145
See application file for complete search history.

(56) References Cited

U.S. PATENT DOCUMENTS

| 5,760,217 A | 6/1998 | Wijesekera et al. |
| 6,603,070 B2 | 8/2003 | Lindsey et al. |
| 2004/0023941 A1 | 2/2004 | Crapo et al. |

OTHER PUBLICATIONS

Clarke et al. "Selective Synthesis of Asymmetrically Substituted 5,15-Diphenylporphyrins" *Tetrahedron Letters* 39:7167-7168 (1998).
Elgie et al. "Application of combinatorial techniques in the synthesis of unsymmetrically substituted 5,15-diphenylporphyrins" *Tetrahedron Letters* 41:2753-2757 (2000).
Hombrecher et al. "Synthese von 5,15-diarylsubstituiertern Porphyrinen Ober Aminomethylierung von Bis(4-ethyl-3-methyl-2-pyrryl)phenylmethanen" *Liebigs Ann. Chem.* 219-227 (1991).
International Search Report and Written Opinion for PCT/US06/25164; date of mailing Feb. 20, 2007.
Love et al. "The syntheses and structures of Group 1 expanded dipyrrolides: the formation of a 12-rung amidolithium circular ladder" *Chem. Commun.* 1682-1683 (2003).
Reid et al. "Double-stranded, [4 +4] helicates of Fe(II) and Mn(II) supported by an extended dipyrrolide ligand" *Dalton Trans.* 4387-4388 (2003).
Schell et al. "Synthesis and Investigation of Glycosylated Mono- and Diarylporphyrins for Photodynamic Therapy" *Bioorganic & Medicinal Chemistry* 7:1857-1865 (1999).
Sutton et al. "Functionalized diphenylchlorins and bacteriochlorins: their synthesis and bioconjugation for targeted photodynamic therapy and tumour cell imaging" *Journal of Porphyrins and Phthalocyanines* 4:655-658 (2000).
Sutton et al. "Porphyrin, Chlorin, and Bacteriochlorin Isothiocyanates: Useful Reagents for the Synthesis of Photoactive Bioconjugates" *Bioconjugate Chem.* 13:249-263 (2002).
International Preliminary Report on Patentability, Search Report and Written Opinion, PCT/US2006/025164, mailed Feb. 7, 2008.

*Primary Examiner* — Paul V. Ward
(74) *Attorney, Agent, or Firm* — Myers Bigel Sibley & Sajovec, P.A.

(57) ABSTRACT

A method of making a porphyrin (I) is carried out by condensing (i) a bis(imino)dipyrromethane of Formula II:

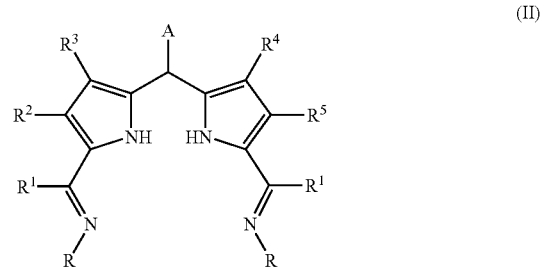

with (ii) a dipyrromethane to produce a reaction product; then (b) optionally oxidizing said reaction product with an oxidizing agent; and then (c) optionally demetallating said reaction product to produce the porphyrin. Methods of making compounds of Formula II are also described.

12 Claims, 3 Drawing Sheets

METHODS AND INTERMEDIATES FOR THE SYNTHESIS OF PORPHYRINS

RELATED APPLICATIONS

This application claims priority to and is a divisional of U.S. patent application Ser. No. 11/193,562, filed Jul. 29, 2005 now U.S. Pat. No. 7,582,751, now allowed, and is related to Jonathan S. Lindsey, Masahiko Taniguchi, and Dazhong Fan, U.S. patent application Ser. No. 11/192,934, Methods and Intermediates for the Synthesis of Porphyrins, filed Jul. 29, 2005, now issued as U.S. Pat. 7,501,508, the disclosure of each of which is incorporated by reference herein in its entirety.

This invention was made with US Government support under Grant Number GM36238 from the National Institutes of Health. The Government has certain rights to this invention.

FIELD OF THE INVENTION

The present invention concerns methods for making porphyrins, including but not limited to trans-A,B-porphyrins, with bis(imine)dipyrromethane intermediates.

BACKGROUND OF THE INVENTION

Porphyrinic macrocycles bearing distinct patterns of substituents are important building blocks in diverse applications. Two distinct strategies have been applied to control the pattern of substituents about the porphyrin perimeter: (1) pre-arranging substituents in precursors to the porphyrinic macrocycle, or (2) preparing a porphyrin with a limited number of substituents and then introducing additional substituents by derivatization of the porphyrin. As an example of the former, the acid-catalyzed condensation of a dipyrromethane-dicarbinol+a dipyrromethane followed by oxidation provides a rational synthesis of ABCD-porphyrins [1]. The derivatization procedures in the latter approach include (i) halogenation of the porphyrin meso position and subsequent C—C bond formation (e.g., Suzuki, Heck, Sonogashira, or related palladium-mediated coupling reactions)[2] or (ii) nucleophilic attack of an alkyl or aryl lithium reagent followed by DDQ oxidation [3].

Porphyrins bearing only one or two meso-substituents (i.e., trans-AB-, trans-$A_2$-, A-porphyrins) are of considerable interest owing to their compact size. A variety of trans-AB-porphyrins have been prepared although most also contain a full complement of β-substituents [4]. Porphyrins bearing only one or two meso substituents and lacking β-substituents in principle are available via the same methodology used to prepare ABCD-porphyrins, but traditionally the syntheses have been carried out by alternative routes. All known routes to trans-AB-, trans-$A_2$-, and A-porphyrins are described below.

trans-AB-porphyrins: Synthetic approaches to β-unsubstituted trans-AB-porphyrins are illustrated based on the synthetic method (statistical or rational) and the substitution pattern of the precursors (Scheme 1, Routes 1-6). Statistical methods (Routes 1 [5] and 2 [6]) do not require functionalization of the dipyrromethane but result in a mixture of three porphyrins that requires chromatographic purification. The [2+2] MacDonald-type condensations of dipyrromethane derivatives include a dipyrromethane-1,9-dicarbinol+a dipyrromethane (Route 3, demonstrated for β-substituted substrates only) [7], a 5-substituted diformyldipyrromethane+a 5-substituted dipyrromethane (Route 4) [8], and a 5-substituted 1,9-bis(hydroxymethyl)dipyrromethane+a 5-substituted dipyrromethane (Route 5) [9]. In each case, the acid catalysis required to facilitate reaction at the α-substituent (e.g., formyl or hydroxymethyl group) often results in undesired rearrangement of the dipyrromethane reactants or oligopyrromethane intermediates, resulting in the formation of undesired porphyrinic macrocycles (i.e., scrambling) [9]. A related route (Route 6) developed in parallel with the work herein employs a 1,9-bis(N,N-dimethylaminomethyl)dipyrromethane+a dipyrromethane [10].

Scheme 1

Statistical Methods

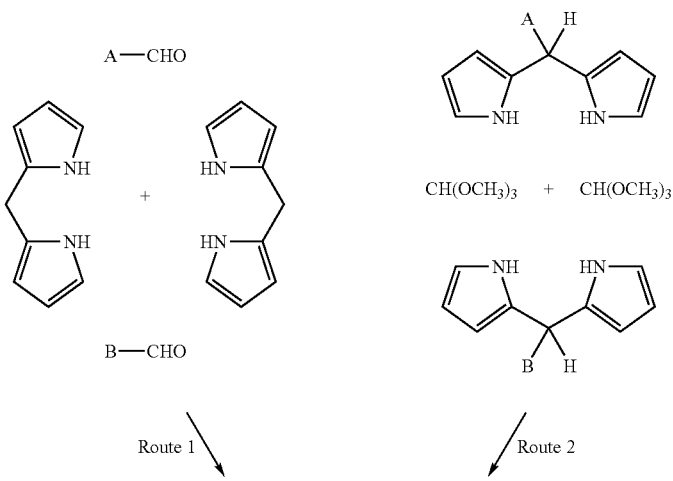

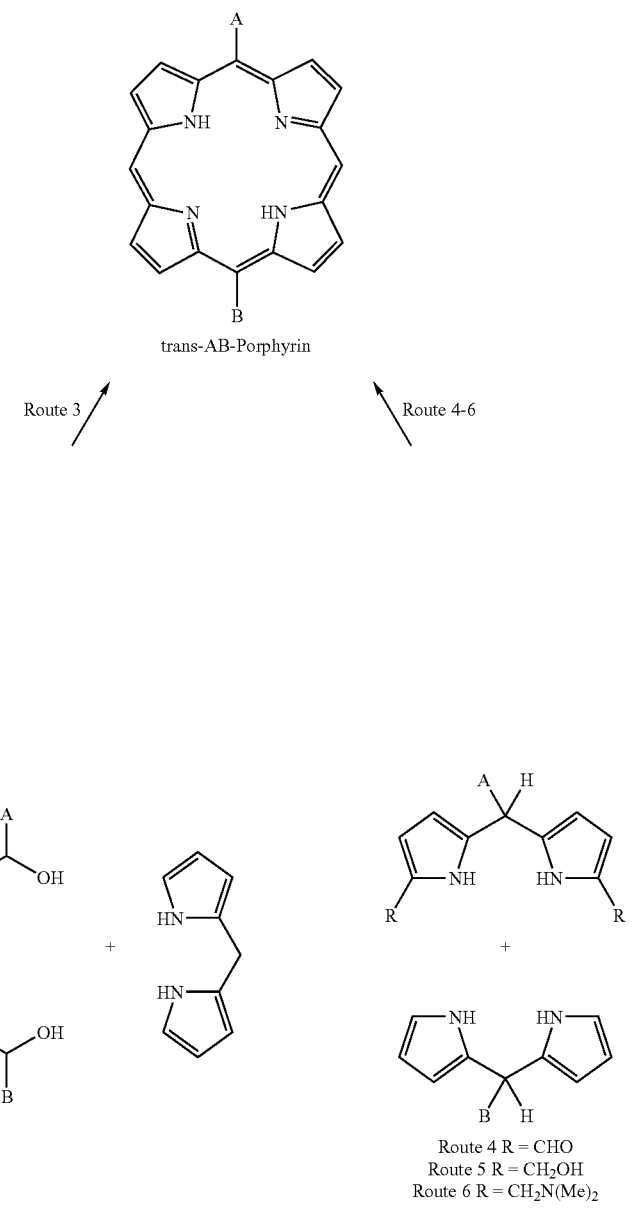

Rational Methods trans-A$_2$-porphyrins: The synthesis of trans-A$_2$-porphyrins can be achieved via the same routes as for trans-AB-porphyrins (where A=B in which case routes 1-5 are all rational) [9, 11, 12], as well as the self-condensation of a dipyrromethane-1-carbinol [12]. The simplest and most effective approach entails route 1, where dipyrromethane itself is reacted with aldehyde A [11].

A-porphyrins: Rational synthetic methods for preparing porphyrins bearing a single meso substituent have been applied exclusively with β-substituted dipyrromethanes (Scheme 2): (1) MacDonald [2+2] condensation of a diformyldipyrromethane+a dipyrromethane (Route 7) [13-15], and (2) a biladiene+aldehyde (Route 8) [15, 16]. A statistical synthesis afforded a β-unsubstituted A-porphyrin in 2-12% yield together with trans-A$_2$-porphyrin byproducts (Route 9) [17]. An alternative approach to introduce a single meso substituent entails substitution of porphine [18, 19]. Porphyrins bearing a single meso substituent also have resulted as byproducts of scrambling processes with meso-unsubstituted dipyrromethanes [20,21] or tripyrrane [19].

Scheme 2
Rational Methods
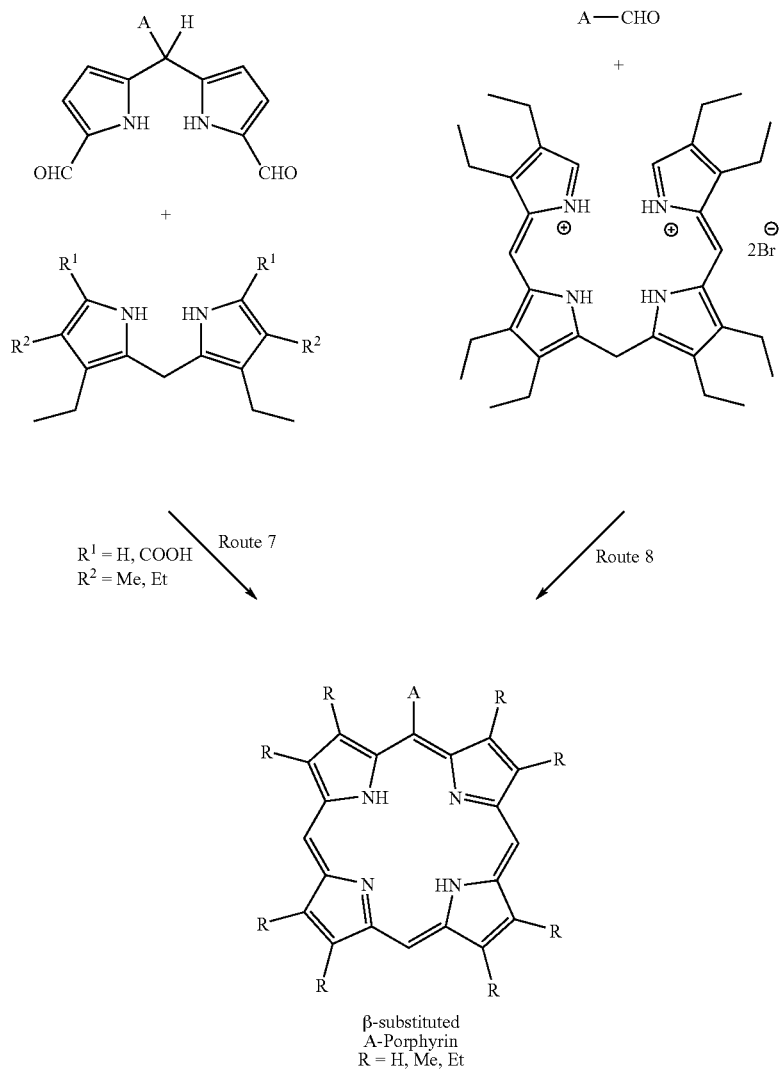
β-substituted
A-Porphyrin
R = H, Me, Et
Statistical Methods
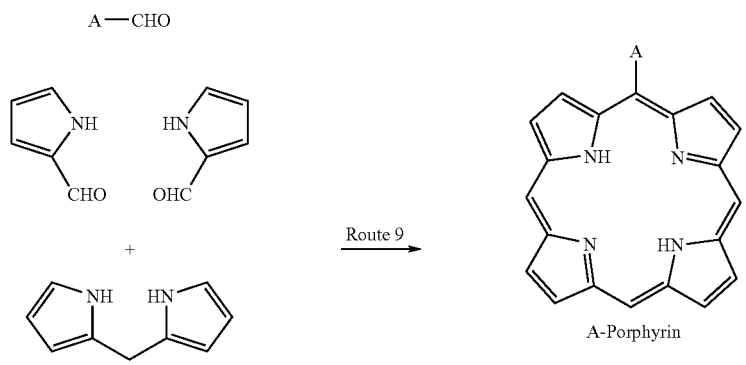
A-Porphyrin In attempting to apply the methodology developed for the synthesis of ABCD-porphyrins to porphyrins bearing lesser substitution (e.g., trans-AB-, A-porphyrins), we were surprised to find that dipyrromethane reactants bearing a primary carbinol (route 5, Scheme 1) resulted in low yields of porphyrin (<5%) and the occurrence of scrambling [9]. By contrast, dipyrromethanes bearing a secondary carbinol (alkyl or aryl) typically afford yields of 10-35% and proceed without scrambling. Although such shortcomings can be circumvented in the synthesis of trans-AB-porphyrins through use of route 3, a number of substituents (mesityl [1], branched alkyl [22]) cannot be accommodated at the carbinol position. Moreover, no such solution is available for the synthesis of A-porphyrins.

We note also that the yields of trans-AB-porphyrins that bear β-substituents are often quite reasonable. The good yields are attributed to the following factors: (1) lack of a meso substituent at the dipyrromethane lessens propensity to scrambling, (2) the presence of β-substituents at the dipyrromethane enforces conformations inclined to cyclize, and (3) blockage of the β-position leaves the α-position as the only site available for reaction. These features are absent in β-unsubstituted trans-AB-porphyrins, and consequently, refined methods are required for preparing this seemingly simple class of compounds.

SUMMARY OF THE INVENTION

A first aspect of the invention is a method of making a porphyrin of Formula I:

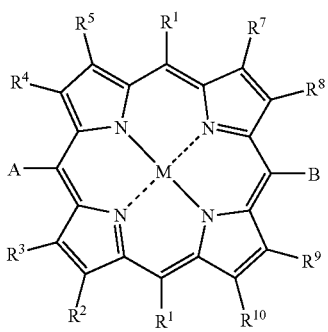

(I)

wherein:

A and B are each independently H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, mercapto, azido, cyano, hydroxyl, nitro, acyl, alkoxy, alkylthio, amino, alkylamino, arylalkylamino, disubstituted amino, acylamino, acyloxy, amide, sulfonamide, urea, alkoxylacylamino, aminoacyloxy, hydrophilic groups, surface attachment groups, cross-coupling groups or bioconjugatable groups;

$R^1$ is selected from the group consisting of H, alkyl and aryl;

$R^2$, $R^3$, $R^4$, $R^5$, $R^7$, $R^8$, $R^9$, and $R^{10}$ are each independently selected from the group consisting of H, halo, loweralkoxy, and loweralkylthio; and M is a metal or a pair of hydrogen atoms;

said method comprising:
(a) condensing (i) a bis(imino)dipyrromethane of Formula II:

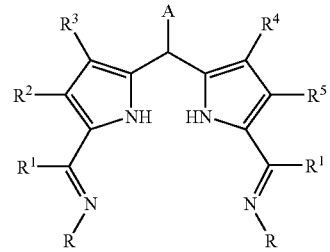

(II)

wherein:

R is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl; and A, $R^1$, $R^2$, $R^3$, $R^4$, and $R^5$ are as given above, with (ii) a dipyrromethane of Formula III:

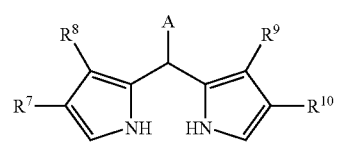

(III)

wherein B, $R^7$, $R^8$, $R^9$ and $R^{10}$ are as given above, in an organic solvent containing a metal salt to produce a reaction product; then (b) optionally oxidizing said reaction product with an oxidizing agent; and then (c) optionally demetallating said reaction product to produce the porphyrin of Formula I.

A further aspect of the invention is a method of making a compound of Formula II:

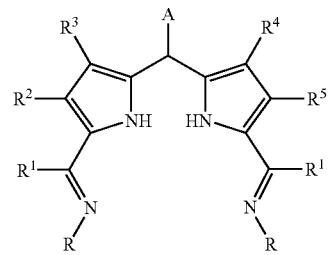

(II)

wherein R, $R^1$, $R^2$, $R^3$, $R^4$, $R^5$ and A are as given above, comprising reacting a dipyrromethane of Formula IV:

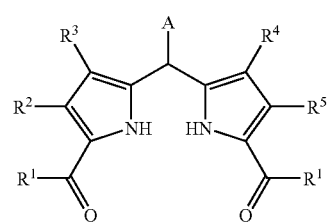

(IV)

wherein A, $R^1$, $R^2$, $R^3$, $R^4$ and $R^5$ are as given above with a compound of Formula V:

$$R-NH_2 \qquad (V)$$

wherein R is as given above in an organic solvent to produce said compound of Formula II.

The foregoing and other objects and aspects of the invention are explained in greater detail in the drawings herein and the specification set forth below.

Figure 1:
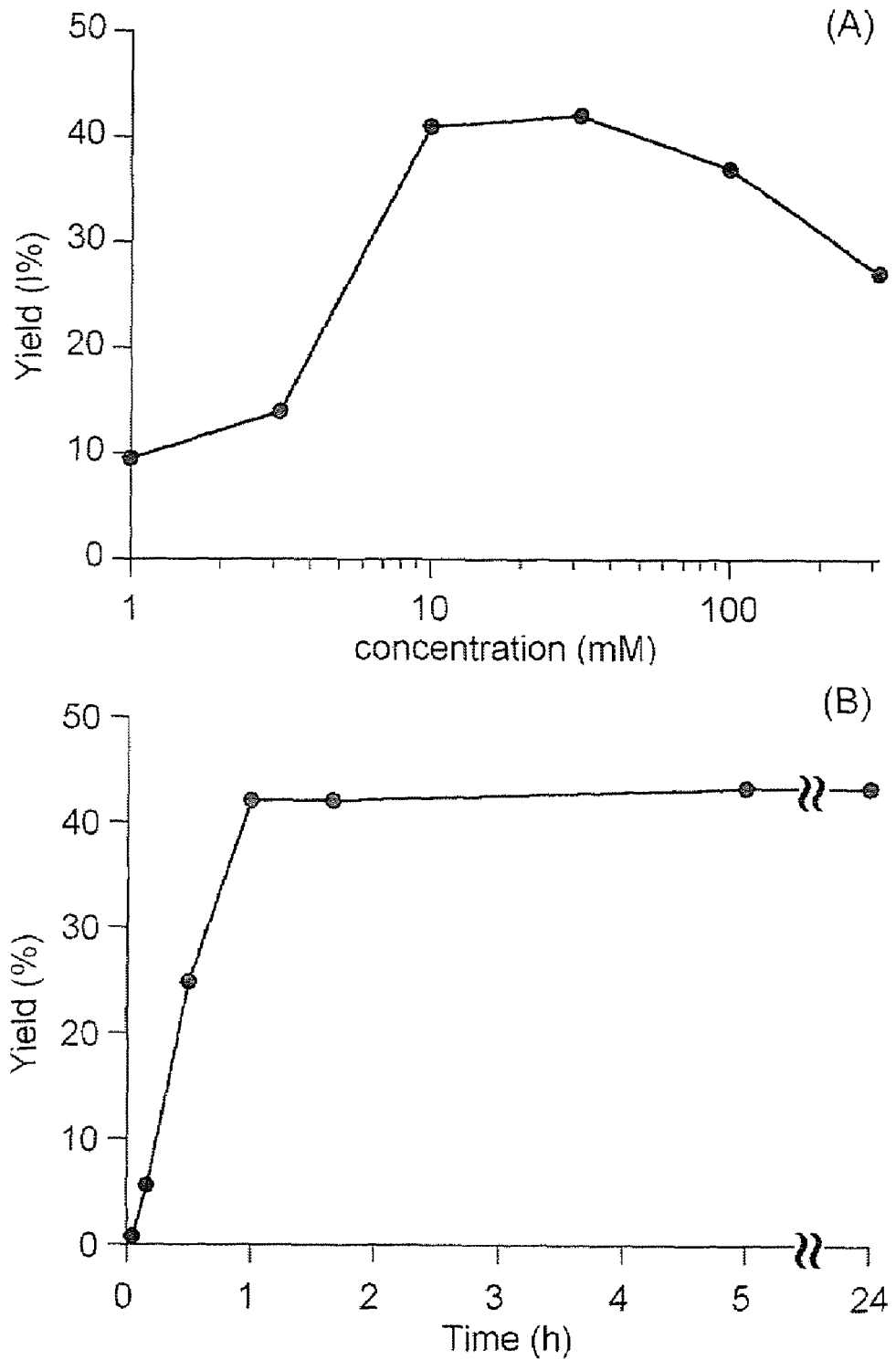
FIG. 1. (A) The effect of the concentration of dipyrromethane species [3a] and [1b] in porphyrin formation [Zn(OAc)$_2$ (10 equiv) in EtOH at reflux in air for 5 h; data points are 1, 3.16, 10, 31.6, 100, and 316 mM]. The yield was determined by absorption spectroscopy in THF. (B) Yield of porphyrin Zn4ab as a function of time upon condensation of 3a+1b{[3a]=[1b]=10 mM, Zn(OAc)$_2$ (10 equiv) in EtOH at reflux in air}. The yield was determined by absorption spectroscopy in THF.

The present invention is explained in greater detail in the specification set forth below.

DETAILED DESCRIPTION OF THE PREFERRED EMBODIMENTS

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10, 20, 40 or 50 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1 or 2.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. "Aryl" includes aromatic heterocyclic groups or heterocyclo groups as discussed below. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Monosubstituted-amino" as used herein alone or as part of another group means the radical —NHR, where R ia selected from the groups alkyl, haloalkyl, alkenyl, alkynyl, cycloalkyl, cycloalkylalkyl, aryl, arylalkyl, heterocyclo, heterocycloalkyl.

"Amine" as used herein refers to amino, monosubstituted-amino, disubstituted-amino.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)$NR_aR_b$ radical, where $R_a$ and $R_b$ are any suitable substituent such as alkyl, cycloalkyl, alkenyl, alkynyl or aryl.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —$N(R_c)C(O)NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —OC(O)$NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aromatic or nonaromatic (e.g., saturated or partially unsaturated aliphatic) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline. tetrahydroisoquinoline, tetrahydroquinoline, thiopyranopyridine, and the like. These rings may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Dipyrromethane" as used herein includes both unsubstituted and substituted dipyrromethanes, which may be unsubstituted or substituted one or more times at the 1, 2, 3, 5, 7, 8 or 9 positions with any suitable substituent such as halo, carbonyl, alkyl, fluoroalkyl including perfluoroalkyl, aryl (e.g., A or B at the 5 position; dialkylaminomethyl alkyl at the 1 and 9 positions), Dipyrromethanes may be coupled to porphyrinic macrocycles at any suitable position on the dipyrromethanes, including the 1, 2, 3, 5, 7, 8, or 9 position, and particularly the 5 position.

"Metal" as used herein is any suitable metal, including but not limited to Cu, Zn, Mg, Pt, Pd. Sn, Ni, and Al.

"Metal salt" as used herein includes but is not limited to zinc, palladium, copper, nickel, or cobalt salts. Zinc salts are currently preferred. The salts may be formed with any suitable counterion(s), including but not limited to acetate, chloride, acac (acetylacetate), etc.

"Surface attachment group" may be any reactive substituent useful for attaching a compound to a substrate such as a metal, insulator, semiconductor substrate or polymer, which reactive substituent may be coupled directly to the parent molecule or coupled to the parent molecule by a linker included as a portion of the surface attachment group. When the linker is aromatic the surface attachment group is said to be aromatic.

"Cross-coupling group" may be any reactive substituent useful for coupling a compound to another compound such as another porphyrin, as a semiconductor substrate or polymer, which reactive substituent may be coupled directly to the parent molecule or coupled to the parent molecule by a linker included as a portion of the cross-coupling group. When the linker is aromatic the cross-coupling group is said to be aromatic.

"Bioconjugatable group" may be any reactive substituent or member of a specific binding pair useful for attaching a compound to another organic compound such as a protein, peptide, nucleic acid (e.g., DNA, RNA), which reactive substituent or member of a specific binding pair may be coupled directly to the parent molecule or coupled to the parent molecule by an linker included as a portion of the bioconjugatable group. When the linker is aromatic the bioconjugatable group is said to be aromatic.

"Hydrophilic group" refers to any aromatic or aliphatic group that is water soluble or enhances the water solubility of the corresponding compound to which it is coupled. Hydrophilic groups may be coupled directly to the parent molecule or coupled to the parent molecule by a linker included as a portion of the hydrophilic group. When the linker is aromatic the bioconjugatable group is said to be aromatic.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

The disclosures of all United States Patent references cited herein are to be incorporated by reference herein as if fully set forth.

A. Surface Attachment Groups.

As noted above, compounds of the invention can be substituted with a surface attachment group, which may be in protected or unprotected form. A surface attachment group may be a reactive group coupled directly to the azolo group, or coupled to the azolo group by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to:

4-carboxyphenyl,
carboxymethyl,
2-carboxyethyl,
3-carboxypropyl,
2-(4-carboxyphenyl)ethynyl,
4-(2-(4-carboxyphenyl)ethynyl)phenyl,
4-carboxymethylphenyl,
4-(3-carboxypropyl)phenyl,
4-(2-(4-carboxymethylphenyl)ethynyl)phenyl;
4-hydroxyphenyl,
hydroxymethyl,
2-hydroxyethyl,
3-hydroxypropyl,
2-(4-hydroxyphenyl)ethynyl,
4-(2-(4-hydroxyphenyl)ethynyl)phenyl,
4-hydroxymethylphenyl,
4-(2-hydroxyethyl)phenyl,
4-(3-hydroxypropyl)phenyl,
4-(2-(4-hydroxymethylphenyl)ethynyl)phenyl;
4-mercaptophenyl,
mercaptomethyl,
2-mercaptoethyl,
3-mercaptopropyl,
2-(4-mercaptophenyl)ethynyl,
4-(2-(4-mercaptophenyl)ethynyl)phenyl,
4-mercaptomethylphenyl,
4-(2-mercaptoethyl)phenyl,
4-(3-mercaptopropyl)phenyl,
4-(2-(4-mercaptomethylphenyl)ethynyl)phenyl;
4-selenylphenyl,
selenylmethyl,
2-selenylethyl,
3-selenylpropyl,
2-(4-selenylphenyl)ethynyl,
4-selenylmethylphenyl,
4-(2-selenylethyl)phenyl,
4-(3-selenylpropyl)phenyl,
4-selenylmethylphenyl,
4-(2-(4-selenylphenyl)ethynyl)phenyl;
4-tellurylphenyl,
tellurylmethyl,
2-tellurylethyl,
3-tellurylpropyl,
2-(4-tellurylphenyl)ethynyl,
4-(2-(4-tellurylphenyl)ethynyl)phenyl,
4-tellurylmethylphenyl,
4-(2-tellurylethyl)phenyl,
4-(3-tellurylpropyl)phenyl,
4-(2-(4-tellurylmethylphenyl)ethynyl)phenyl;
4-(dihydroxyphosphoryl)phenyl,
(dihydroxyphosphoryl)methyl,
2-(dihydroxyphosphoryl)ethyl,
3-(dihydroxyphosphoryl)propyl,
2-[4-(dihydroxyphosphoryl)phenyl]ethynyl,
4-[2-[4-(dihydroxyphosphoryl)phenyl]ethynyl]phenyl,
4-[(dihydroxyphosphoryl)methyl]phenyl,
4-[2-(dihydroxyphosphoryl)ethyl]phenyl,
4-[2-[4-(dihydroxyphosphoryl)methylphenyl]ethynyl]phenyl;
4-(hydroxy(mercapto)phosphoryl)phenyl,
(hydroxy(mercapto)phosphoryl)methyl,
2-(hydroxy(mercapto)phosphoryl)ethyl,
3-(hydroxy(mercapto)phosphoryl)propyl,
2-[4-(hydroxy(mercapto)phosphoryl)phenyl]ethynyl,
4-[2-[4-(hydroxy(mercapto)phosphoryl)phenyl]ethynyl]phenyl,
4-[(hydroxy(mercapto)phosphoryl)methyl]phenyl,
4-[2-(hydroxy(mercapto)phosphoryl)ethyl]phenyl,
4-[2-[4-(hydroxy(mercapto)phosphoryl)methylphenyl]ethynyl]phenyl;
4-cyanophenyl,
cyanomethyl,
2-cyanoethyl,
3-cyanopropyl, 2-(4-cyanophenyl)ethynyl,
4-[2-(4-cyanophenyl)ethynyl]phenyl,
4-(cyanomethyl)phenyl,
4-(2-cyanoethyl)phenyl,
4-[2-[4-(cyanomethyl)phenyl]ethynyl]phenyl;
4-cyanobiphenyl;
4-aminophenyl,
aminomethyl,
2-aminoethyl,
3-aminopropyl,
2-(4-aminophenyl)ethynyl,
4-[2-(4-aminophenyl)ethynyl]phenyl,
4-aminobiphenyl;
4-formylphenyl,
4-bromophenyl,
4-iodophenyl,
4-vinylphenyl,
4-ethynylphenyl,
4-allylphenyl,
4-[2-(trimethylsilyl)ethynyl]phenyl,
4-[2-(triisopropylsilyl)ethynyl]phenyl,
4-(4,4,5,5-tetramethyl-1,3,2-dioxaborolan-2-yl)phenyl;
formyl,
bromo,
iodo,
bromomethyl,
chloromethyl,
ethynyl,
vinyl,
allyl;
4-(ethynyl)biphen-4'-yl,
4-[2-(triisopropylsilyl)ethynyl]biphen-4'-yl,
3,5-diethynylphenyl;
4-(bromomethyl)phenyl, and
2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir*, 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science*, 2001, 494, 1-20; Whitesell, J. K.; Chang, H. K. *Science*, 1993, 261, 73-76; Galoppini, E. et al. *J. Am. Chem. Soc.* 2002, 67, 7801-7811; Siiman, O. et al. *Bioconjigate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl]methyl}phenyl,
1,1,1-tris[4-dihydroxyphosphorylmethyl)phenyl]methyl, and
4-{1,1,1-tris[4-(dihydroxyphosphorylmethyl)phenyl]methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4' -yl, Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc., Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4' -yl etc., Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl, 4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

B. Cross-Coupling Groups.

Compounds produced of the present invention, as individual ring systems or as constituents of sandwich coordination compounds, can be coupled together as linear polymers in like manner as described in U.S. Pat. No. 6,777,516 to Li, Gryko and Lindsey. Examples of suitable linking or cross-coupling groups include but are not limited to groups $J^2$ and $J^3$ below, which may be linked directly to the compound of the invention or by an intervening linker L. Linkers L can be aryl, alkyl, heteroaryl, heteroalkyl (e.g., oligoethylene glycol), peptide, polysaccharide, etc. The cross-coupling group may be simply a reactive attachment group or moiety (e.g., —R' where R' is a reactive group such as bromo), or may comprise a combination of an intervening linker group coupled to a reactive group (e.g., —R"R', where R' is a reactive group and R" is an intervening group such as a hydrophilic group).

Particular examples of linkers include, but are not limited to, 4,4'-diphenylethyne, 4,4'-diphenylbutadiyne, 4,4'-biphenyl, 1,4-phenylene, 4,4'-stilbene. 1,4-bicyclooctane, 4,4'-azobenzene, 4,4'-benzylideneaniline, and 4,4"-terphenyl.

Dyads. The synthesis of dyads of compounds of the invention can proceed via several different types of reactions. The reactions of interest include Glaser (or Eglinton) coupling of two identical porphyrins (generating a butadiyne linker), Cadiot-Chodkiewicz coupling of two porphyrins (generating a butadiyne linker), Sonogashira coupling of two different porphyrins (generating an ethyne linker), Heck or Wittig reactions of two different porphyrins (generating an alkene linker), Suzuki coupling of two different porphyrins (generating a phenylene or biphenyl linker), etc. Other reactions can also be employed.

| $J^1$-L-TD-L-$J^2$ + $J^3$-L-TD-L-$J^4$ | | |
|---|---|---|
| $J^2$ | $J^3$ | Reaction Type |
| —B(OH)$_2$ | —Cl, —Br, —I | Suzuki |
| ═══—H | —Cl, —Br, —I | Sonogashira |

-continued

| $J^1$-L-TD-L-$J^2$ + $J^3$-L-TD-L-$J^4$ | | |
|---|---|---|
| $J^2$ | $J^3$ | Reaction Type |
| ═══—H | ═══—H | Glaser |
| ═══—H | ═══—X | Cadiot-Chodkiewicz |
| —CHO | —Br, —I | Wittig |
| —HC═CH$_2$ | —Br, —I | Heck |

Polymers. The methods for synthesis of polymeric arrays of compounds include but are not restricted to use of the following types of reactions:

Glaser (or Eglinton) coupling of a monomeric porphyrins (generating a butadiyne linker)

Cadiot-Chodkiewicz coupling of two different compounds (generating a butadiyne linker joining a block copolymer)

Sonogashira coupling of two different compounds (generating an ethyne linker joining a block copolymer)

Heck or Witting reactions of two different compounds (generating an alkene linker joining a block copolymer)

Suzuki coupling of two different compounds (generating a phenylene or biphenyl linker joining a block copolymer)

We also can polymerize compounds bearing substituents such as two or more thiophene groups (generating an oligothiophene linker) or two or more pyrrole groups (generating a polypyrrole linker).

The synthesis of the polymers can be performed using stepwise methods or using polymerization methods. Both methods generally require two reactive groups attached to the porphyrin in order to prepare a polymer where the porphyrins are integral components of the polymer backbone. (An alternative design yields pendant polymers where the porphyrins are attached via one linkage to the polymer backbone.) The stepwise synthetic method generally requires the use of protecting groups to mask one reactive site, and one cycle of reactions then involves coupling followed by deprotection. In the polymerization method no protecting groups are employed and the polymer is prepared in a one-flask process.

The polymerizations can take place in solution or can be performed with the polymer growing from a surface. The polymerization can be performed beginning with a solid support as in solid-phase peptide or DNA synthesis, then removed. purified, and elaborated further for specific applications. The polymerization can also be performed with the nascent polymer attached to an electroactive surface, generating the desired electronic material in situ.

C. Bioconjugatable Groups.

Biconjugatable groups may be included in compounds of the invention to provide a reactive site for conjugation so that the compounds may be coupled to or conjugated to other groups, such as proteins, peptides, targeting agents such as antibodies, polymers, particles such as nanoparticles, organic, polymeric or inorganic beads, other solid support surfaces, etc, to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidium, pyridinium). Bioconjugatable groups include amines (including amine derivatives) such as isocyanates, isothiocyanates, iodoacetamides, azides, diazonium salts, etc. acids or Acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212,093; and 6,208,553.

Conjugates. Other groups can be attached to the compounds of the invention to form a conjugate by means of a cross-coupling group or bioconjugatable group to tune or adjust the solubility properties of the compound, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acid may be attached by means of the linking group. Particles such as nanoparticles, glass beads, etc. may be attached by means of the linking group. Where such additional compounds are attached to form a conjugate thay may be attached directly to the compound or attached by means of an intervening group such as a hydrophilic group, depending upon the particular linking group employed (as noted above).

Hydrophilic groups. Compounds of the present invention may include hydrophilic groups coupled thereto as groups A and/or B, e.g., covalently coupled thereto directly or by an intervening linker, to facilitate delivery thereof, or improve stability, in accordance with known techniques. Suitable hydrophilic groups are typically polyols or polyalkylene oxide groups, including straight and branched-chain polyols, with particular examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

D. Reactions.

As noted above, the present invention provides a method of making a porphyrin of Formula I:

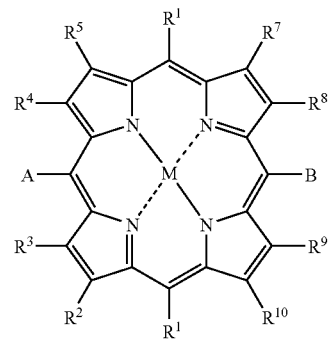

wherein:

A and B are each independently is selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, mercapto, azido, cyano, hydroxyl, nitro, acyl, alkoxy, alkylthio, amino, alkylamino, arylalkylamino, disubstituted amino, acylamino, acyloxy, amide, sulfonamide, urea, alkoxylacylamino, aminoacyloxy, hydrophilic groups, surface attachment groups, cross-coupling groups and bioconjugatable groups (with A preferably aryl, including aromatic hydrophilic groups, aromatic surface attachment groups, aromatic cross-coupling groups, and aromatic bioconjugatable groups);

$R^1$ is selected from the group consisting of H, alkyl and aryl (preferably H);

$R^2$, $R^3$, $R^4$, $R^5$, $R^7$, $R^8$, $R^9$, and $R^{10}$ are each independently selected from the group consisting of H, halo, loweralkoxy, and loweralkylthio; and M is a metal or a pair of hydrogen atoms;

said method comprising:

(a) condensing (i) a bis(imino)dipyrromethane of Formula II:

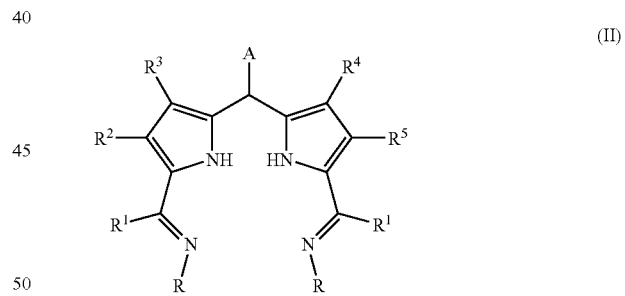

wherein:

R is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl; and A, $R^1$, $R^2$, $R^3$, $R^4$, and $R^5$ are as given above, with (ii) a dipyrromethane of Formula III:

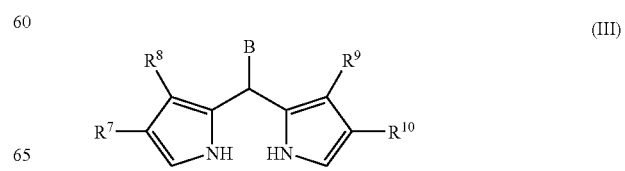

wherein B, $R^7$, $R^8$, $R^9$ and $R^{10}$ are as given above, in a polar or nonpolar, protic or aprotic organic solvent containing a metal salt to produce a reaction product; then (b) optionally oxidizing said reaction product with an oxidizing agent; and then (c) optionally demetallating said reaction product to produce the porphyrin of Formula I. The reaction conditions are not critical and any suitable solvent can be used, including but not limited to methanol, ethanol, propanol, isopropanol, chloroform. tetrahydrofuran, dichloromethane, toluene, and mixtures thereof. The reaction can be carried out at any convenient temperature such as between 0 and 100° C. Any suitable metal salt can be used, including but not limited to zinc, palladium, copper, nickel and cobalt salts (which then provides the metal M for the compound of Formula I). For some substituents no external oxidizing agent is required and oxidation is achieved by oxygen in ambient air. When an oxidizing agent is required any suitable oxidizing agent can be used, such as oxygen or a quinone oxidizing agent such as dichlorodicyanobenzoquinone (DDQ), p-chloranil, and o-chloranil. The demetallating step can be carried out in accordance with known techniques by treating or mixing the metallated compound with any suitable acid (e.g., acetic acid, trifluoroacetic acid, hydrochloric acid, sulfuric acid, etc.).

In some embodiments A is preferably an aromatic, or aryl, group, including aromatic hydrophilic groups, aromatic surface attachment groups, aromatic cross-coupling groups, or aromatic bioconjugatable group (for example, an aryl-containing linker group substituted one or more timeswith an alkene, alkyne, alcohol, thiol, selenyl, phosphono, carboxylic acid, formyl, halo or amine group).

In some embodiments, B is preferably a hydrophilic group, surface attachment group, cross-coupling group, or bioconjugatable group (e.g., an alkene, alkyne, alcohol, thiol, selenyl, phosphono, carboxylic acid, formyl, halo or amine group, coupled directly to the parent molecule or by means of an intervening linker group).

In some embodiments, A is a bioconjugatable group and B is a hydrophilic group as given above; or A is a hydrophilic group and B is a biconjugatable group as given above.

The present invention also provides a method of making a compound of Formula II:

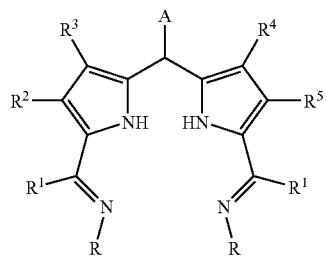

(II)

wherein:

R, is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl;

$R^1$ is H, alkyl or aryl, preferably H;

$R^2$, $R^3$, $R^4$, and $R^5$ are each independently selected from the group consisting of H, halo, loweralkoxy, and loweralkylthio; and A is as given above, preferably aryl.

The method comprises reacting a dipyrromethane of Formula IV:

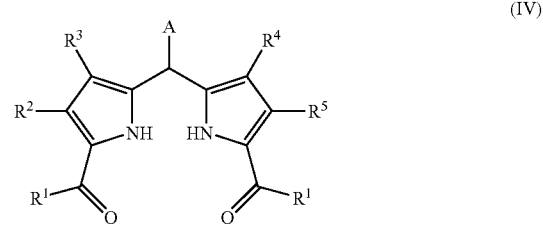

(IV)

wherein A, $R^1$, $R^2$, $R^3$, $R^4$ and $R^5$ are as given above, with a compound of Formula V:

$$R-NH_2 \qquad (V)$$

wherein R is as given above in an organic solvent to produce said compound of Formula II. The reaction conditions are not critical and can be carried out in any suitable organic solvent (such as described above), neat if desired, at any convenient temperature such as 0 to 100° C. The compound of Formula V is preferably included in a stoichiometric amount, preferably in excess, for example five, ten or twenty times excess. Suitable solvents include but are not limited to methylene chloride, chloroform, tetrahydrofuran, nitromethane, toluene, acetonitrile, methanol, ethanol, and mixtures thereof.

Compounds of Formula IV and Formula V can be made in accordance with known techniques for the synthesis of dipyrromethanes and amines, or variations thereof that will be apparent to persons skilled in the art.

E. Utility.

Porphyrins produced by the methods and intermediates described herein are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Compounds produced by the methods and intermediates of the invention are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The compounds can be coupled to substrates to form molecular batteries, molecular capacitors and electrochromic displays as described in U.S. Pat. No. 6,777,516 to Li et al. The porphyrin may comprise a member of a sandwich coordination compound in the information storage molecule, such as described in U.S. Pat. No. 6,212,093 to Li et al., U.S. Pat. No. 6,451,942 to Li et al., or U.S. Pat. No. 6,777,516 to Li et al.

Porphyrins produced by the methods of the invention are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al.

The present invention is explained in greater detail in the following non-limiting Examples.

EXAMPLES

Imine groups have been briefly described as $C_1$ synthons for the synthesis of $A_4$-porphyrins by the condensation of an aldimine with pyrrole [23]. Bis(imino)dipyrromethane derivatives are readily available from the corresponding diformyldipyrromethane by imination with amines [24], and have been used as precursors for expanded porphyrins [25] or as pyrrole-based ligands in metal-directed self-assembly processes [24, 26]. However, bis(imino)dipyrromethanes have not been used for the synthesis of porphyrins as described herein.

Part I below describes synthesis, including the preparation of bis(imino)dipyrromethanes, development of the dipyrromethane+bis(imino)dipyrromethane condensation, and preparation of a set of trans-AB-porphyrins. Part II below describes observations and studies concerning the course of the reaction and intermediates formed with the bis(imino) dipyrromethanes.

Part I. Synthesis

Synthesis of 5-substituted dipyrromethanes. Dipyrromethanes 1a-1 have been prepared previously by a variety of procedures [1, 21, 22, 27-33]. A one-flask solventless synthesis of meso-substituted dipyrromethanes enables direct purification by recrystallization (without aqueous/organic extraction, chromatography, or distillation) [34]. Following this procedure, condensation of the desired aldehyde (paraformaldehyde, in case of 1j) and pyrrole (100 equiv) at room temperature using $InCl_3$ ($MgBr_2$ for 1c) followed by recrystallization afforded multi-gram quantities of the desired meso-substituted dipyrromethanes 1a-1 in yields of 14-88% (Chart 1). Dipyrromethane 1k was prepared by a reported procedure [21]. Dipyrromethanes 1g, 1h, 1i, and 1l were purified by chromatography. The purity of each dipyrromethane was >97% as determined by GC-FID analysis.

Synthesis of 1,9-diformyldipyrromethanes. Vilsmeier formylation [35] is an established method for preparing 1,9-diformyldipyrromethanes. A diacyldipyrromethane-tin complexation strategy facilitates isolation and purification of the 1,9-diacyldipyrromethane, which otherwise are poorly crystalline and chromatograph with difficulty [36]. Thus, Vilsmeier formylation of dipyrromethanes (1a, 1c, 1d, 1f, 1h) followed by treatment with TEA and n-$Bu_2SnCl_2$ in $CH_2Cl_2$ afforded the crude dibutyltin complex. Purification by filtration through a pad of silica followed by treatment with diethyl ether/methanol afforded the dibutyltin complexes as pink solids in 46-67% yield (dibutyltin complex $Bu_2Sn$-2h was obtained as a brown viscous liquid, Table 1). Our attempts to remove the color by further purification (column chromatography, repeated recrystallization, treatment with activated carbon) proved unsuccessful. However, elemental analysis of each tin complex corresponded well with the calculated value.

CHART 1

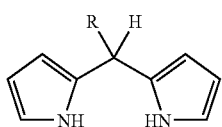

1a-I a
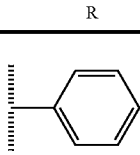

CHART 1-continued

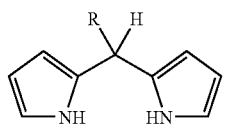

1a-I

R b
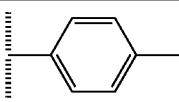

c
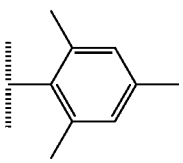

d
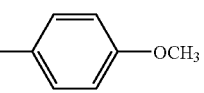

e
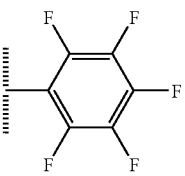

f
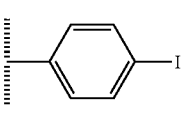

g
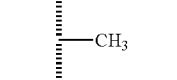

h
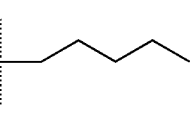

i
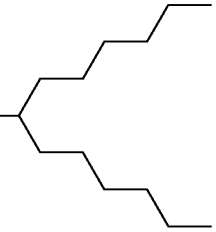

j
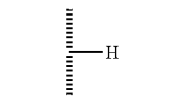

k
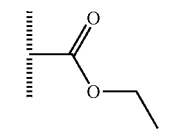

CHART 1-continued

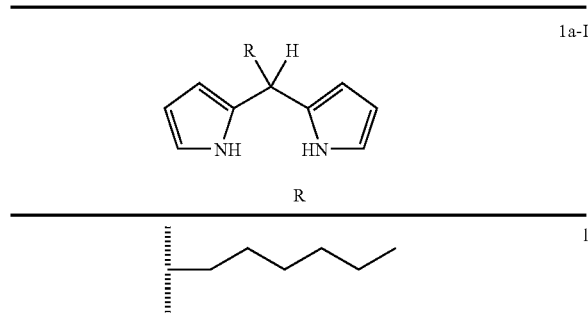

Decomplexation with TFA furnished the corresponding 1,9-diformyldipyrromethanes (2a [12], 2d [14], 2f) as off-white solids, and 2h was obtained as a brown viscous liquid in 72-86% yields. The overall yield of 1,9-diformylation was 30-46%. The separation of 2c and the tin byproduct from the reaction mixture proved difficult; therefore, 2c was used for further reaction without demetalation (vide infra). 1,9-Diformyl-5-(pentafluorophenyl)dipyrromethane (2e), 1,9-diformyl-5-methydipyrromethane (2g), 1,9-diformyl-5-(tridec-7-yl)dipyrromethane (2i), and 1,9-diformyldipyrromethane (2j) [37] were purified without using the tin-complexation method.

Synthesis of 1,9-Bis(imino)dipyrromethanes with diverse imino substituents. 1,9-Diformyldipyrromethane 2a was condensed with a set of amines to give the corresponding 1,9-bis(imino)dipyrromethanes as summarized in Table 2. $^1$H NMR spectroscopy enabled determination of the ratio of diformyl-dipyrromethane 2a: formyl-iminodipyrromethane:bis(imino)dipyrromethane in the reaction mixture by using the peak from the 5-position proton of dipyrromethane species (e.g., 2a, 5.20 ppm; mono-imino species, 5.27 ppm; 3a-Ph, 5.32 ppm).

TABLE 1

Synthesis of 1,9-diformyldipyrromethanes

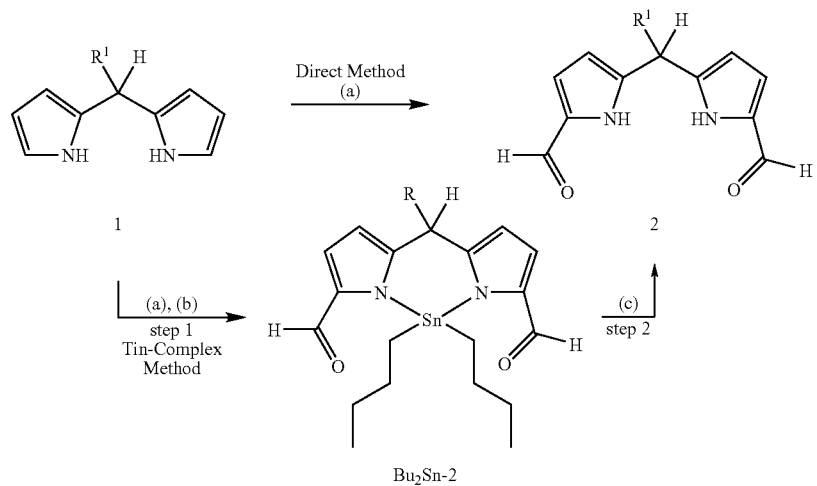

| | | | | Yield (%)[b] | | |
|---|---|---|---|---|---|---|
| | | | direct | tin-complexation method | | |
| Entry | R | | method | step 1 | step 2 | total |
| 1 | a | (phenyl) | NA[c] | 58 | 79 | 46 |
| 2 | b | (mesityl) | NA | 67 | —[d] | —[d] |
| 3 | d | (4-methoxyphenyl) | NA | 53 | 82 | 38 |

TABLE 1-continued
| | | | b | | | |
|---|---|---|---|---|---|---|
| 4 | e | 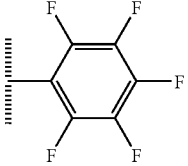 | 85 | NA | NA | NA |
| 5 | f | 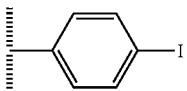 | NA | 46 | 86 | 40 |
| 6 | g |  | 78 | NA | NA | NA |
| 7 | h | 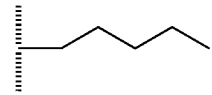 | 72 | 42 | 72 | 30 |
| 8 | i | 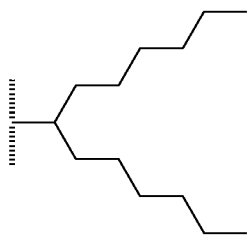 | 47 | NA | NA | NA |
| 9 | j |  | 70 | NA | NA | NA |
[a] Reaction conditions: (a) DMF, POCl$_3$, at room temperature for 1 h; (b) Bu$_2$SnCl$_2$ (1 equiv) and triethylamine (3 equiv) in CH$_2$Cl$_2$ at room temperature for 20 min to 1 h; (c) TFA in CH$_2$Cl$_2$ at room temperature for 10 min.
[b] Isolated yield.
[c] Not attempted.
[d] Not successful; see text.

TABLE 2

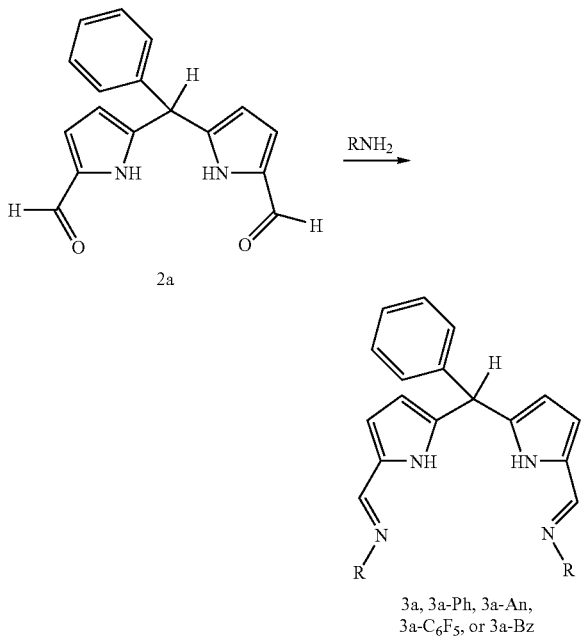

3a, 3a-Ph, 3a-An,
3a-C$_6$F$_5$, or 3a-Bz

Reaction conditions for imine formation with different amines[a]

| Entry | R | equiv of amine | Temp. | Time (h) | % Yield[b] 2a | Monoimine | Bis(imine) |
|---|---|---|---|---|---|---|---|
| 1 | n-Pr- | 2.1 | rt | 24 | 0 | 3 | 97 (3a) |
| 2 | n-Pr- | 20 | rt | 1 | 0 | 0 | 100 (3a) |
| 3 | PhCH$_2$— | 2.1 | rt | 2 | Trace | <5 | >95 (3a-Bz) |
| 4 | p-anisyl- | 2.1 | rt | 1 | 0 | 18 | 82 (3a-An) |
| 5 | p-anisyl- | 2.1 | reflux | 1 | 0 | 6 | 94 (3a-An) |
| 6 | Ph- | 2.1 | reflux | 20 | 0 | 19 | 81 (3a-Ph) |
| 7 | Ph- | 20 | rt | 1 | 0 | 9 | 91 (3a-Ph) |
| 8[c] | Ph- | 20 | rt | 1 | 0 | Trace | >99 (3a-Ph) |
| 9 | C$_6$F$_5$— | 2.1 | reflux | 24 | 60 | 40 | 0 (3a-C$_6$F$_5$) |
| 10 | C$_6$F$_5$— | 20 | reflux | 24 | 10 | 53 | 37 (3a-C$_6$F$_5$) |
| 11[d] | C$_6$F$_5$— | 2 | rt | 0.5 | 23 | 57 | 20 (3a-C$_6$F$_5$) |

[a]Reaction conditions: The amine was added to a THF solution of 2a (300 mM).
[b]The yields of imine were assessed by $^1$H NMR spectroscopy.
[c]Aniline was used as a solvent.
[d]TFA (2 equiv) was included.

The reaction of 2a and n-propylamine proceeded smoothly at room temperature, affording bis(imine) 3a quantitatively (Entry 1). A simple method to obtain analytically pure bis(imine) 3a entailed stirring diformyldipyrromethane 2a and excess n-propylamine for 1 h at room temperature, followed by removal of excess n-propylamine (bp=48° C.) in vacuo (Entry 2). The resulting bis(imine) 3a could be used for porphyrin formation without further purification. Benzylamine reacted similarly with 2a, affording 3a-Bz (Entry 3). p-Anisidine or aniline reacted with diformyldipyrromethane 2a to give bis(imine) 3a-An or 3a-Ph (Entries 4-8), though reaction was facilitated with heating or excess amine. The synthesis of bis(imine) 3a-C$_6$F$_5$ required the use of TFA as a catalyst and resulted in recovery of the starting diformyldipyrromethane 2a (Entries 9-11). The separation of 3a-C$_6$F5 by chromatography was not successful. In summary, the reactivity of amines parallels their solution basicity: n-propylamine~benzylamine>p-anisidine>aniline>>2,3,4,5,6-pentafluoroaniline.

Optimization of reaction conditions for porphyrin formation via 1,9-bis(imino)dipyrromethanes. The [2+2] condensation of a 1,9-bis(imino)dipyrromethane+a dipyrromethane was optimized with respect to imine substituent, reagents, solvent, concentration, and time. To screen a large number of different reaction conditions, porphyrin-forming reactions were performed on a small scale. The yields of porphyrin were calculated using absorption spectroscopy by removing small aliquots from the reaction mixture, assuming $\epsilon_{Soret}$=500,000 M$^{-1}$ cm$^{-1}$. The spectroscopic yields and isolated yields corresponded well (vide infra). Samples from the crude reaction mixture were examined by laser-desorption mass spectrometry (LD-MS) [38] to assess the level of scrambling [39]. The extent of scrambling was categorized as Level 0 (no detectable scrambling) to Level 4 (complete scrambling) as described previously [39].

(i) Imine substituents. The effects of N-imino substituents on porphyrin formation were examined by carrying out the reaction of 1b+3a, 3a-Ph, 3a-An, or 3a-Bz (Table 3). The reaction with 3a or 3a-Bz afforded porphyrin Zn4ab in yield of up to 40% without use of DDQ. The reaction proceeded in higher yield at reflux versus room temperature. No porphyrin byproducts (i.e., scrambling) were observed (Entries 1-4).

The reaction of 3a-Ph also proceeded without detectable scrambling, but DDQ was required as an oxidant (Entries 5 and 6). On the other hand, the reaction of 3a-An+1b required DDQ and afforded porphyrin with the formation of scrambled byproducts (Entries 7 and 8). Thus, oxidation was achieved aerobically with the alkylimino substituents whereas DDQ was necessary with arylimino substituents.

The straightforward synthesis and purification of 3a prompted us to use the propyl group as an imino substituent for further studies. To understand the robustness of the reaction conditions, the effects of reagents, solvent, concentration, and time were investigated using the reaction of 3a+1b as a standard. The results are as follows (spectroscopic yields):

(ii) Solvent. Seven solvents of diverse polarity and composition were examined (Table 4). Porphyrin was formed in each solvent without detectable scrambling. The highest yield (44%) was obtained in EtOH.

TABLE 3

Effects of N-imine substituents in formation of porphyrin Zn4ab[a]

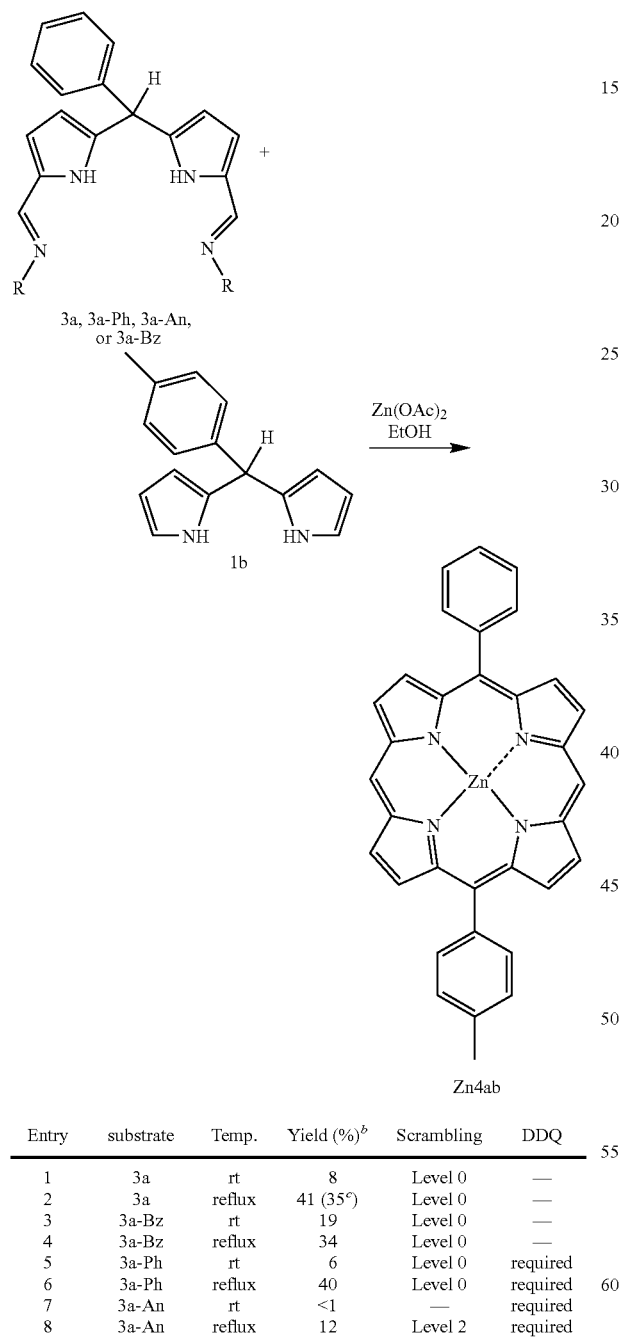

| Entry | substrate | Temp. | Yield (%)[b] | Scrambling | DDQ |
| --- | --- | --- | --- | --- | --- |
| 1 | 3a | rt | 8 | Level 0 | — |
| 2 | 3a | reflux | 41 (35[c]) | Level 0 | — |
| 3 | 3a-Bz | rt | 19 | Level 0 | — |
| 4 | 3a-Bz | reflux | 34 | Level 0 | — |
| 5 | 3a-Ph | rt | 6 | Level 0 | required |
| 6 | 3a-Ph | reflux | 40 | Level 0 | required |
| 7 | 3a-An | rt | <1 | — | required |
| 8 | 3a-An | reflux | 12 | Level 2 | required |

[a]Reaction conditions; [3a, 3a-Ph, 3a-An, 3a-Bz] and [1b] = 10 mM, Zn(OAc)$_2$ (10 equiv) in EtOH at room temperature (20 h) or under reflux (18 h), then treated with 3 mol equiv of DDQ (for 3a-Ph and 3a-An; Entries 3-6).
[b]The yields of porphyrin were determined using absorption spectroscopy.
[c]Isolated yield.

TABLE 4

Effect of solvent in formation of porphyrin Zn4ab[a]

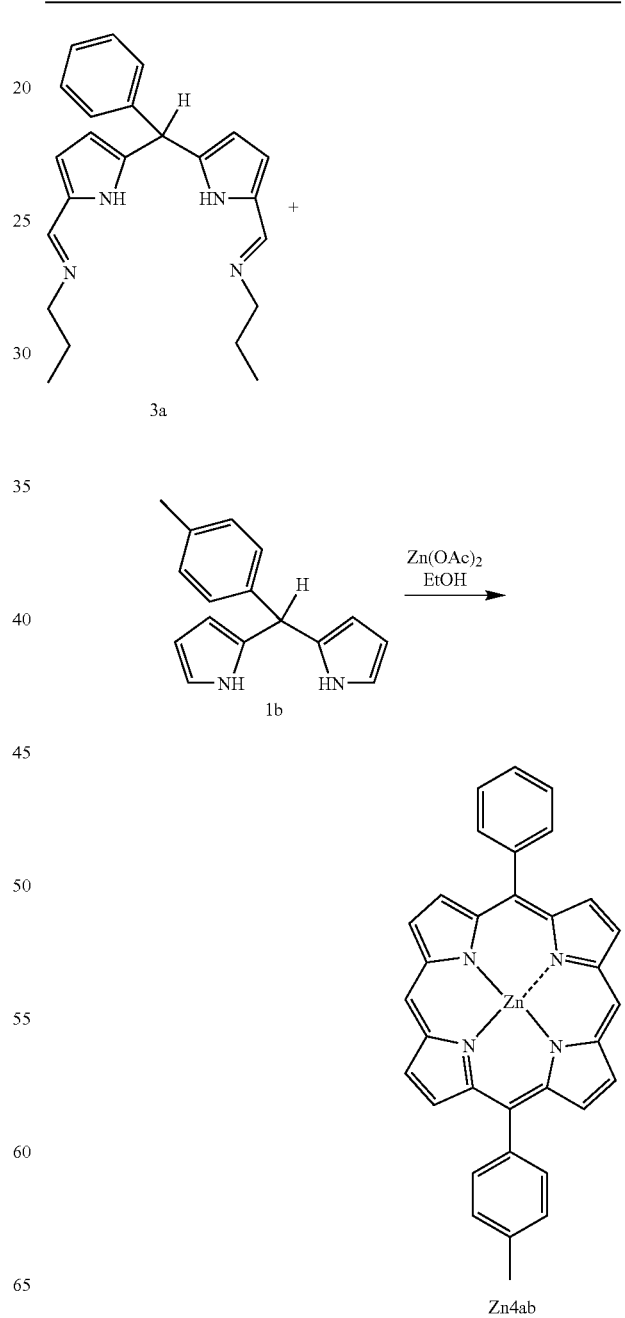

TABLE 4-continued

| Entry | Solvent | Yield (%)[b] room temperature | reflux |
|---|---|---|---|
| 1 | Toluene | 6 | 41 |
| 2 | $CH_2Cl_2$ | 10 | 36 |
| 3 | $CHCl_3$ | 4 | 37 |
| 4 | THF | 1 | 9 |
| 5 | EtOH | 9 | 44 |
| 6 | MeOH | 9 | 27 |
| 7 | $CH_3CN$ | 2 | 27 |

[a]Reaction conditions; [3a] and [1b] = 10 mM, $Zn(OAc)_2$ (10 equiv) in each solvent at room temperature (20 h) or under reflux (5 h).
[b]The yields of porphyrin were determined using absorption spectroscopy.
No scrambling was observed in each reaction (LD-MS analysis).

(iii) Reagents. The highest yield of porphyrin was obtained when 10 equiv of $Zn(OAc)_2$ was used. The yield was 10% when a stoichiometric amount of $Zn(OAc)_2$ was used. Other metal reagents [$Cu(OAc)_2$, $Pd(OAc)_2$, $MgBr_2$, or $Yb(OTf)_3$] in place of $Zn(OAc)_2$ resulted in a low or negligible yield of porphyrinic species. Attempts to use a Brønsted acid (TFA or acetic acid) to facilitate reaction at room temperature did not afford porphyrin.

(iv) Temperature.

The reaction at room temperature gave the porphyrin in 8% yield (16-24 h) versus ~40% upon reflux (Table 4).

(v) Concentration. The effects of reactant concentration were examined over the range from 1 mM to 316 mM. The amount of $Zn(OAc)_2$ was changed commensurably with reactant concentration. The highest yield (~41% spectroscopic yield) was obtained at 10 mM and 31.6 mM (FIG. 1-A). The yield declined to 28% at the highest concentration examined (316 mM). The lack of a precipitous decline at high concentration indicates the applicability of this method for large-scale synthetic applications.

(vi) Reaction time. The yield of porphyrin as a function of time with 31.6 mM reactants is shown in FIG. 1-B. The formation of porphyrin Zn4ab is essentially complete within 1 h.

(vii) Aeration. Small-scale reactions were carried out in a closed vessel containing sufficient headspace to provide more than a stoichiometric quantity of air for the oxidation. Large-scale reactions were carried out with gentle aeration of the reaction vessel such that significant evaporation of the solvent was not observed. Porphyrin formation was complete within 5 h.

On the basis of these studies, the best conditions for porphyrin formation were identified as follows: [3a] and [1b] =10 or 31.6 mM with $Zn(OAc)_2$ (100 mM or 316 mM) in EtOH under reflux exposed to air (or gentle aeration) for 5-24 h. The reaction mixture was quite clean and the porphyrin was readily purified. Examination of the crude reaction mixture by LD-MS did not show the presence of any other porphyrin species.

Exploration of scope (i) Survey of diverse trans-AB-porphyrins. The optimized conditions were applied to the synthesis of various porphyrins (Scheme 3, Table 5). Emphasis was placed on (1) variation of the substituents, (2) assessment of any scrambling processes, and (3) yields of porphyrin. Altogether, the preparation of 28 trans-AB-porphyrins, 8 trans-$A_2$-porphyrins, and 8 A-porphyrins was examined. The 1,9-bis(imino)dipyrromethanes (3a, 3c-j) were easily prepared as described above and readily characterized by $^1$H NMR spectroscopy. The imination was insensitive to the nature of the 5-substituents of 1,9-diformyl-dipyrromethanes and was typically complete within 30 min.

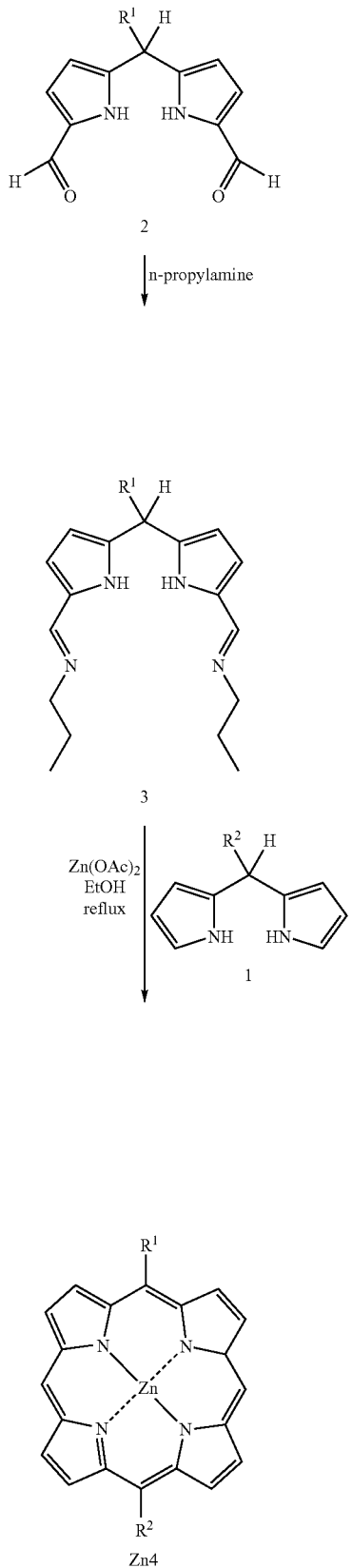

Scheme 3

TABLE 5

Survey of the formation of trans-AB-, A2—, and A-porphyrins[a]

| | | 3a (phenyl) | 3c (mesityl) | 3d (4-methoxyphenyl) | 3e (pentafluorophenyl) |
|---|---|---|---|---|---|
| 1a | phenyl | 42 | 26 | 32 | 33 |
| 1c | mesityl | 36 | iS | 26 | 21 |
| 1d | 4-methoxyphenyl | 30 | 22 | 32 | 26 |
| 1e | pentafluorophenyl | 23 | 13 | 25 | 15 |
| 1f | 4-iodophenyl | 35 | 24 | 31 | 25 |
| 1g | methyl | 30 | 28 | 30 | 30 |
| 1h | n-pentyl | 33 | 24 | 31 | 28 |
| 1i | di(n-hexyl)methyl | 25 | 19 | 19 | 20 |
| 1j | H | 31 | 27 | 30 | 28 |

| | | 3f (4-iodophenyl) | 3g CH₃ | 3h n-pentyl | 3i di(n-hexyl)methyl | 3j H |
|---|---|---|---|---|---|---|
| 1a | phenyl | 39 | 1 | 0 | 2 | 0 |
| 1c | mesityl | 27 | <1 | 0 | 3 | 0 |

TABLE 5-continued

| | | | | | | |
|---|---|---|---|---|---|---|
| 1d | 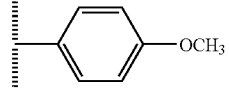 —OCH₃ | 30 | <1 | 0 | 1 | 0 |
| 1e | 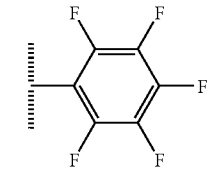 (pentafluorophenyl) | 20 | <1 | 0 | 1 | <1 |
| 1f | 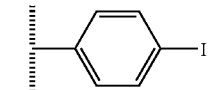 —I | 29 | <1 | 0 | 2 | 0 |
| 1g | methyl | 32 | <1 | 0 | 2 | 1 |
| 1h | n-pentyl | 30 | <1 | 0 | 2 | 1 |
| 1i | 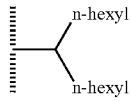 n-hexyl / n-hexyl | 23 | <1 | 0 | 2 | <1 |
| 1j | H | 30 | 1 | <1 | 1 | 2 |

[a]The yields of porphyrin were determined by absorption spectroscopy of small aliquots from the reaction mixture. All reactions with yields >5% gave level 0 scrambling (detected by LD-MS analysis); scrambling could not be assessed reliably for the low-yielding reactions exhibited by 3g-j. Reaction conditions: 10 mM reactants and 10 equiv of Zn(OAc)₂ in EtOH under reflux exposed to air for 2 h.

In each case, a mixture of dipyrromethane and 1,9-bis(imino)dipyrromethane was treated with Zn(OAc)₂ (10 equiv) in ethanol, with concentrations of [3]=[1]=10.0 mM. The reaction mixture was refluxed for 2 h. The yields of porphyrin were determined spectroscopically and ranged from <1% to 42% depending on the substituents and combination of the dipyrromethane precursors. Each crude reaction mixture was examined for the presence of scrambled porphyrin species and none was detected. Note that a given porphyrin can be made in two ways by switching the combination of the 1,9-bis(imino)dipyrromethane (3) and dipyrromethane (1). Regardless of the combination, the resulting porphyrinogen should be identical; thus, differences in porphyrin yields should reflect reactivity during the condensation rather than oxidation (vide infra).

The 1,9-bis(imino)dipyrromethanes substituted with an aromatic group at the 5-position (3a, 3c-f) reacted with dipyrromethanes having an aryl, alkyl, or no substituent at the 5-position, affording the respective porphyrin in 13-42% yield. Porphyrin formation proceeded well regardless of the presence of electron-donating groups (4-methoxyphenyl, 1d or 3d) or electron withdrawing groups (pentafluorophenyl, 1e or 3e) in either the dipyrromethane or the 1,9-bis(imino)dipyrromethane unit.

To our surprise, attempts to use the 1,9-bis(imino)dipyrromethanes 3g-i (meso-alkyl) and 3j (meso-H) in reactions with dipyrromethanes resulted at best in only a trace of porphyrin. Spectral examination of the crude mixture showed the formation of a zinc complex of the 1,9-bis(imino)dipyrromethane as well as the presence of the unreacted dipyrromethane (See Part II). Attempts were made to improve the yield of the alkyl/alkyl substituted trans-AB-porphyrins exemplified for the reaction of 3h+1a by examination of diverse reaction conditions. (1) Acid catalysis: Attempts to use a Brønsted acid (TFA or acetic acid) did not afford porphyrin. (2) Solvent: Replacement of ethanol (bp 78° C.) with 1-butanol (bp 116-118° C.) or 1-pentanol (bp 136-138° C.) under refluxing conditions gave no change in the yield of porphyrin. Use of solvents of diverse polarity and composition (listed in Table 4) did not improve the yield of porphyrin. Note that 1,9-bis(imino)dipyrromethanes were readily soluble in ethanol regardless of the nature of the 5-substituent; thus, the solubility of 1,9-bis(imino)dipyrromethanes is not a source of the poor reactivity. (3) Oxidant: Attempts to oxidize the reaction mixture with DDQ or p-chloranil gave no porphyrin, suggesting the failure originated in the condensation yielding porphyrinogen rather than the oxidation of the porphyrinogen.

In short, the bis(imino)dipyrromethane+dipyrromethane method is not suitable for the synthesis of alkyl/alkyl substituted trans-AB-porphyrins or alkyl substituted A-porphyrins. By contrast, porphyrin formation proceeded smoothly (19-32%) when the same meso-H and meso-pentyl substituents were attached to the dipyrromethane unit and an aryl substituent was present at the 5-position of the bis(imino)dipyrromethane.

(ii) Direct synthesis of porphyrins from 1,9-bis(imino)dipyrromethane-tin complexes. A streamlined synthesis was examined by direct imination of the 1,9-diformyldipyrromethane-tin complex, thereby avoiding the TFA-induced decomplexation step (Scheme 4). The reaction of tin complex Bu₂Sn-2a and n-propylamine proceeded smoothly at room temperature over 2 h to give 3a in quantitative yield. This direct imination method may be useful in cases where exposure to Brønsted acids needs to be minimized. The formation of the bis(imino)dipyrromethane species was readily assessed by ¹H NMR spectroscopy, monitoring the disappearance and appearance of the resonances due to the aldehyde (9.14 ppm) and imino (7.95 ppm) groups, respectively, over the course of 2 h. After imination, the crude sample of 3a was reacted with 1b, affording Zn4ab in 30% spectroscopic yield. The yield was slightly lower than that with the imination of the uncomplexed diformyldipyrromethane (37%); however, the lower yield is offset by the omission of one step in the sequence. The dibutyltin byproducts present in the crude reaction mixture after imination have little consequence on porphyrin formation other than the minor decrease in yield.

Scheme 4

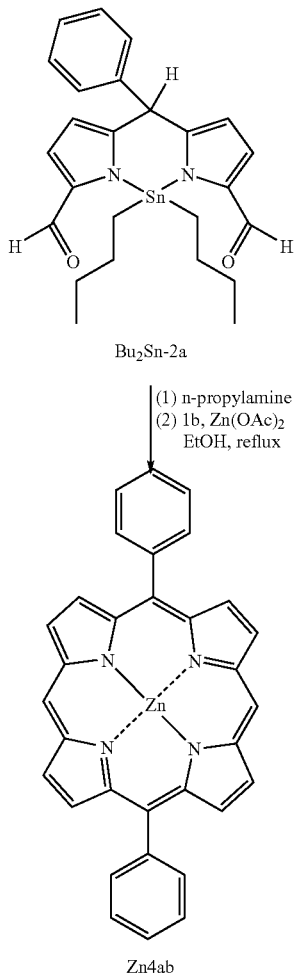

This approach was applied with Bu$_2$Sn-2c. The reaction of tin complex Bu$_2$Sn-2c and n-propylamine proceeded smoothly at room temperature and 3c was obtained quantitatively as evidenced by $^1$H NMR spectroscopy. The resulting crude sample of 3c was reacted with dipyrromethanes 1a,c-j to form the corresponding zinc porphyrins in yields of 19-32% (Table 5).

(iii) Preparative synthesis of porphyrins. A series of trans-AB-, trans-A$_2$-, and A-porphyrins bearing diverse substituents was prepared and isolated (Table 6). In each case, examination of the crude reaction mixture showed no detectable scrambling. Each porphyrin was purified in a straightforward manner by passage over a short pad of silica. The isolated yields (30-38%) of the trans-AB-porphyrins are comparable to the spectroscopic yields (Table 5, 35-42%). To establish a benchmark for comparison with reactions of bis(imino)dipyrromethanes versus diformyldipyrromethanes, the condensation of 1,9-diformyldipyrromethane 2a+the dipyrromethane 1b was examined, which afforded trans-AB-porphyrins Zn4ab in 6% yield (Entry 2). The synthesis of porphyrins by reaction of a 1,9-diformyldipyrromethane+a dipyrromethane in the presence of p-toluenesulfonic acid and zinc acetate also has been described [8].

Aerobic oxidation. The observation that porphyrin formation can be achieved aerobically (without use of a quinone oxidant such as DDQ or p-chloranil) is somewhat surprising. Typically, the direct aerobic oxidation of porphyrinogens only can be achieved at high temperature [40]. Oxidation at more modest temperatures (including room temperature) can be achieved aerobically in the presence of oxygen-activation catalysts [41], or anaerobically with quinone oxidants [42]. The key difference here is that the porphyrinogen formed from reaction of a bis(imino)dipyrromethane+dipyrromethane is expected to bear an alkylamino group at each of the 5- and 15-positions, rather than more typical hydrocarbon substituents.

TABLE 6

Synthesis of trans-AB, trans-A$_2$, and A-porphyrins$^a$

| Entry | R$^1$ | R$^2$ | Porphyrin (Type) | Yield (%)$^b$ |
|---|---|---|---|---|
| 1 | 3a | 1b (phenyl) | Zn4ab (AB) | 37 |
| 2 | 2a (diformyl species) | 1b (phenyl) | Zn4ab (AB) | 6 |
| 3 | 3d (4-methoxyphenyl) | 1e (pentafluorophenyl) | Zn4de (AB) | 30 |

TABLE 6-continued

Synthesis of trans-AB, trans-A$_2$, and A-porphyrins[a]

| Entry | R$^1$ | | R$^2$ | | Porphyrin (Type) | Yield (%)[b] |
|---|---|---|---|---|---|---|
| 4 | 3e | 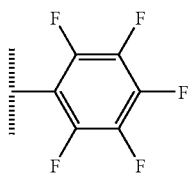 | 1d | 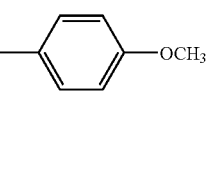 | Zn4de (AB) | 32 |
| 5 | 3f | 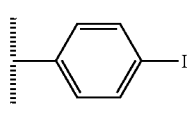 | 1k | 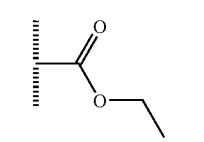 | Zn4fk (AB) | 38 |
| 6 | 3a | 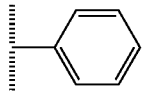 | 1a | 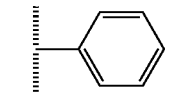 | Zn4aa (A$_2$) | 36 |
| 7 | 3c | 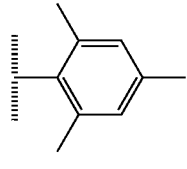 | 1j | 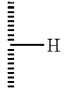 | Zn4cj (A) | 38 |
| 8 | 3a | 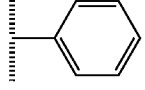 | 1h | 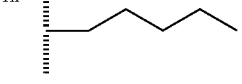 | Zn4ah (AB) | 32 |

[a]Reactions were performed at 0.1-0.5 mmol scale. Reaction conditions: [3] and [1] = 31.6 mM ([2] and [1] = 10 mM for Entry 2), Zn(OAc)$_2$ (10 equiv) in refluxing ethanol exposed to air (18 h). All reactions give level 0 scrambling (assessed by LD-MS analysis).
[b]Isolated yields.

The putative 5,15-bis(alkylamino)porphyrinogen is shown in Scheme 5 for the reaction of the free-base precursors dipyrromethane 1 and bis(imino)dipyrromethane 3. Elimination of the amines (loss of 2 RNH$_2$) transforms the porphyrinogen (a hexahydroporphyrin) to a dihydroporphyrin. The latter apparently undergoes facile oxidation with ½O$_2$ to give the porphyrin with formation of one equivalent of H$_2$O. Zinc insertion may occur upon formation of the free base porphyrin or at an earlier stage in the process. Although this picture provides a partial explanation of the observed results, further studies are required to identify why aliphatic amines afford conversion without a quinone oxidant while those with aniline are less inclined toward this conversion. One possibility is that the greater basicity of the aliphatic amines versus aromatic amines facilitates complexation or protonation, in turn yielding a better leaving group.

Scheme 5

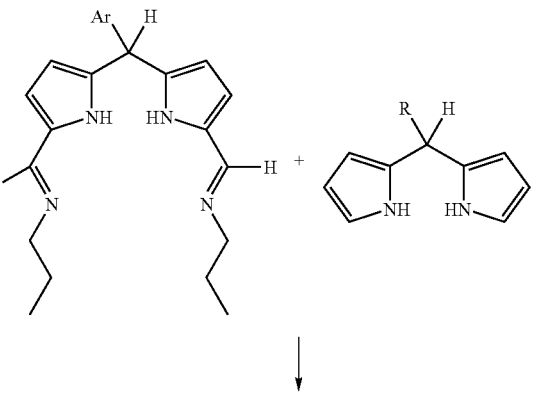

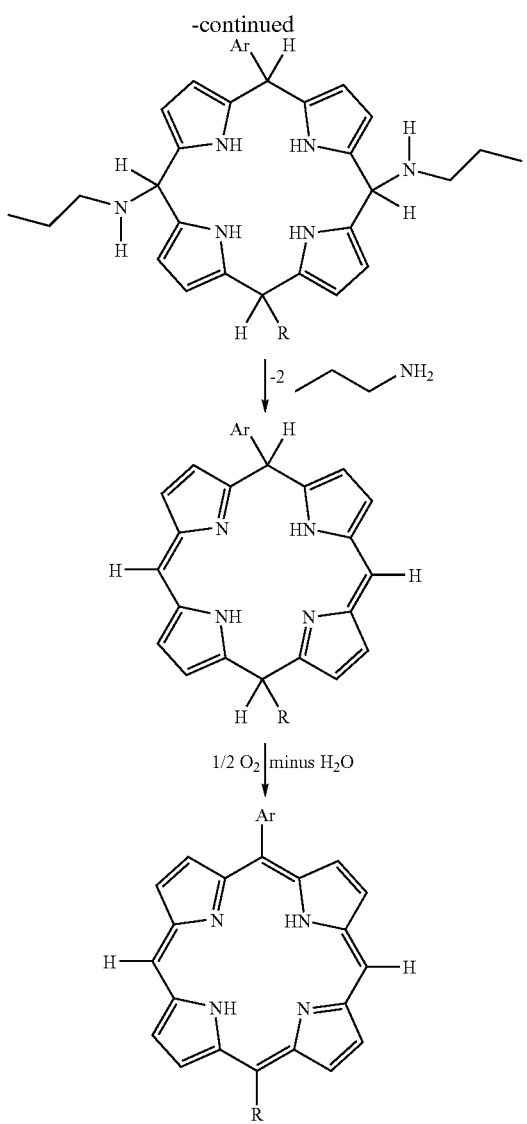

Part II. Reaction course. We made a number of observations concerning the conversion of a bis(imino)dipyrromethane+a dipyrromethane to the porphyrin. Two key observations were as follows: (1) For alkyl or H-substituted bis(imino)dipyrromethanes, which did not afford porphyrins, peaks in the higher mass region were observed (m/z=692.3 for H-substituted 3j; m/z=832.6 for pentyl-substituted 3l). (2) The crude reaction mixture of a porphyrin-forming reaction exhibits the peak expected for the zinc porphyrin (e.g., m/z=538.5 for Zn4ab, derived from 3a+1b), and, when the reaction is performed at higher concentration, a similar unexpected set of peaks at higher mass (m/z=844.0). Upon workup, the isolated porphyrin gave only the expected molecule ion peak.

Figure 2:
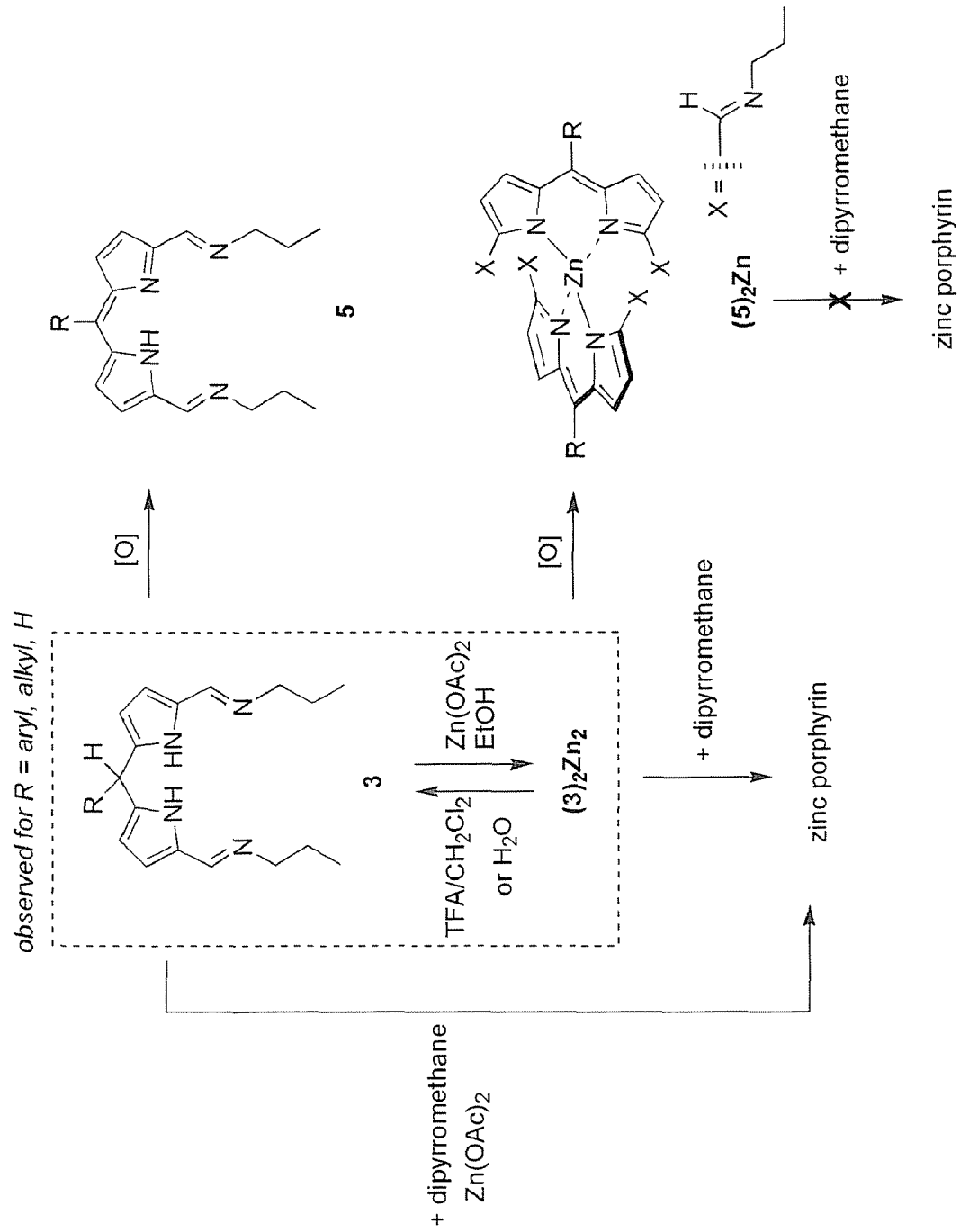
FIG. 2. Reaction intermediates observed on the basis of studies with phenyl (3a), H (3j), and pentyl (3l) substituted bis(imino)dipyrromethanes. All bis(imino)dipyrromethanes examined undergo reversible formation of the complex $(3)_2Zn_2$. Those bis(imino)dipyrromethanes bearing aryl (but not alkyl or H) groups undergo the processes shown outside the dashed box. Note that simple chromatographic purification afforded the desired zinc porphyrin (4) free of reactants (3+dipyrromethane) and any intermediates or byproducts such as 5, $(3)_2Zn_2$, and $(5)_2Zn_2$.

A lengthy study was performed to understand whether the observed results could explain the disparate reactivity of the aryl- versus alkyl- or H-substituted bis(imino)dipyrromethanes. A framework for presentation of the results is provided in FIG. 2. The key results from the studies are as follows:

(1) The bis(imino)dipyrromethane reacts rapidly with zinc acetate to give a dimer composed of two bis(imino)dipyrromethanes and two zinc atoms, $(3)_2Zn_2$, which accounts for the unexpected peaks in the mass spectrum.

(2) The dimer $(3)_2Zn_2$ forms reversibly, regardless of the nature of the meso substituent (aryl, alkyl, H), and undergoes facile disassembly upon exposure to water or trace acid. The complex derived from a 5-aryl-substituted bis(imino)dipyrromethane, e.g., $(3a)_2Zn_2$, reacts with a dipyrromethane, either directly or via the uncomplexed species 3a, to give the porphyrin.

(3) $^1$H NMR examination of the crude reaction mixture with an alkyl-substituted bis(imino)dipyrromethane (3g) revealed that the dipyrromethane counterpart (1a) remained intact and unreacted.

(4) The pale orange solution of a bis(imino)dipyrromethane (3) bearing an aryl (but not alkyl or H) substituent slowly turns purple upon standing overnight. The color change stems from the conversion of aryl-substituted bis(imino)dipyrromethane to the corresponding dipyrrin (e.g., 3a→5a). The bis(imino)dipyrromethane complex with zinc, $(3a)_2Zn_2$, can undergo oxidation to the corresponding bis[bis(imino)dipyrrin]zinc comple, $(5a)_2Zn$, which does not react with a dipyrromethane to give the porphyrin.

The key studies that led to these results are summarized below, and additional information is provided in the Experimental Section.

Figure 3:
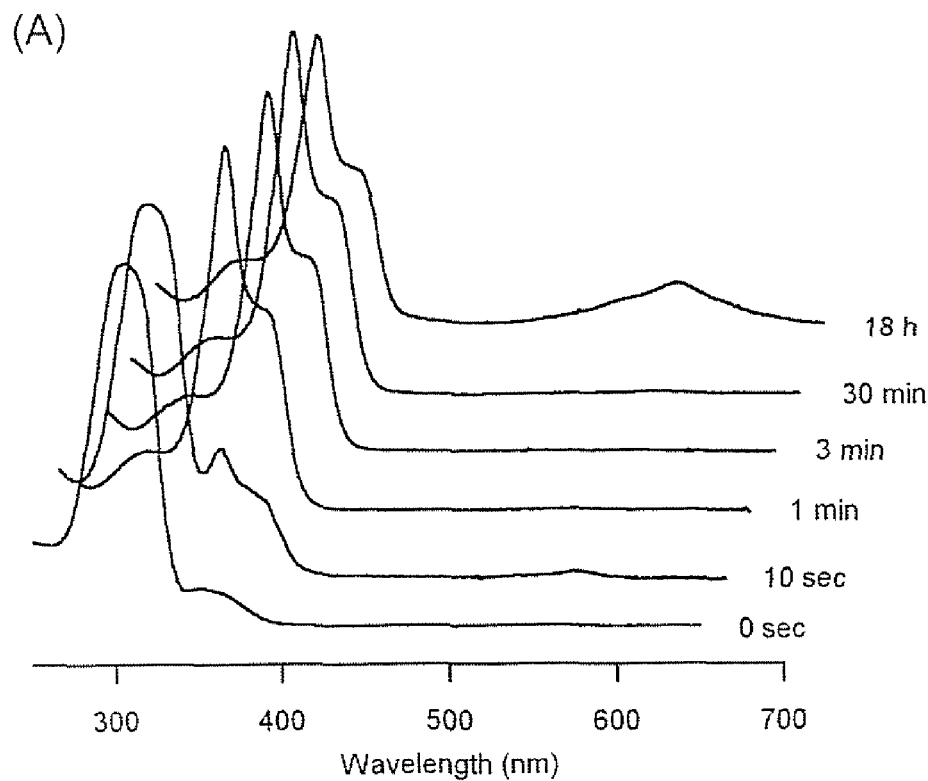
FIG. 3. Absorption spectral traces of the reaction of 3a (31.6 mM) upon treatment with Zn(OAc)$_2$ (10 equiv) in ethanol. (A) Reaction at room temperature, showing predominant formation of $(3a)_2Zn_2$ within 1 min. (B) Reaction at reflux, showing formation of $(3a)_2Zn_2$ and conversion largely to bis(dipyrrinato)zinc(II) complex $(5a)_2Zn$. Note that the amount of bis(dipyrrinato)zinc(II) complex $(5a)_2Zn$ can be quite small despite the intense color of the mixture, due to the sizable molar absorption coefficient expected for such species [43].
Figure 3:
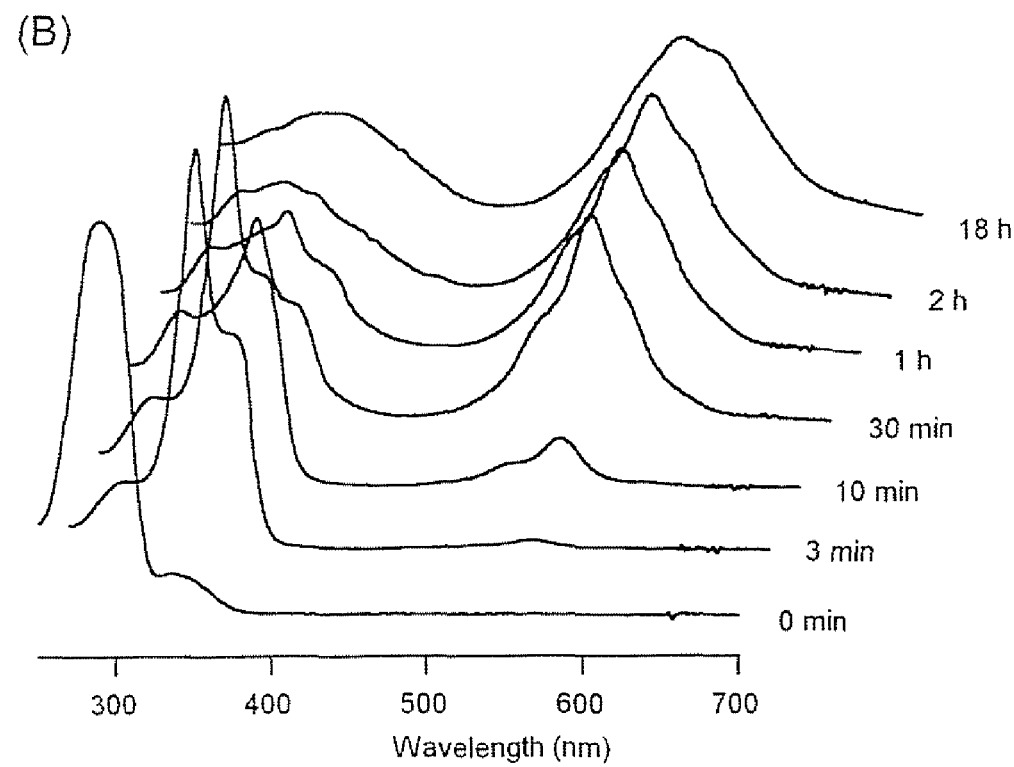

Formation of $(3a)_2Zn_2$. Bis(imino)dipyrromethane 3a was treated with Zn(OAc)$_2$ in ethanol at room temperature in the absence of a dipyrromethane. The reaction was followed by absorption spectroscopy, $^1$H NMR spectroscopy, and LD-MS analysis. The vivid pink mixture formed immediately gave an unexpected peak at m/z=844.0, which is assigned to the complex composed of two bis(imino)dipyrromethanes and two zinc atoms: $(3a)_2Zn_2$. The formation of $(3a)_2Zn_2$ was essentially complete within 1 min at room temperature as shown by absorption spectroscopy (FIG. 3). The absence of a peak in the ~450-520 nm region characteristic of dipyrrin species [43] indicates that $(3a)_2Zn_2$ contains the dipyrromethane, not dipyrrin, framework. In general, each of the bis(imino)dipyrromethanes that was examined (3a, 3j, 3l) was observed to form the corresponding $(3)_2Zn_2$ complex.

Formation of $(5a)_2Zn$. On standing for a prolonged period (18 h), at room temperature, the initial pink mixture containing $(3a)_2Zn_2$ slowly turned deep purple owing to the formation of $(5a)_2Zn$. The purple color stems from the appearance of a new absorption band at 545 nm characteristic of bis(dipyrrinato)Zn(II) complexes. LD-MS analysis gave a new peak at m/z=777.4 (consistent with a complex derived from two molecules of bis(imino)dipyrrin 5a and one zinc atom: 778.3 Da). The conversion of $(3a)_2Zn_2$ to bis(dipyrrinato)Zn(II) complex $(5a)_2Zn$ was more pronounced when the reaction of 3a+Zn(OAc)$_2$ (which quantitatively gave $(3a)_2Zn_2$ in 1 min) was carried out under reflux (FIG. 3B). After 2 h, the absorption band corresponding to $(3a)_2Zn_2$ had disappeared. Also, the conversion of $(3a)_2Zn_2$ to $(5a)_2Zn$ is not entirely clean: upon refluxing $(3a)_2Zn_2$ in EtOH (31.6 mM) in air for 2 days, $(5a)_2Zn$ was formed in >50% (but not quantitative) yield owing to the concomitant formation of high molecular weight material.

It is noteworthy that similar treatment of complex $(3j)_2Zn_2$ did not give an oxidized species analogous to $(5j)_2Zn$. These observations show a correlation between the ease of oxidation of $(3)_2Zn_2$ and the ease of formation of the porphyrin from this complex. Why this should be the case remains unclear.

Structure of complexes $(3)_2Zn_2$. The proposed structure for $(3a)_2Zn_2$ is helical wherein each zinc atom is bonded to two pyrrolic nitrogen atoms (on distinct dipyrromethanes) and coordinated to the $N_{imino}$ atoms (not shown). Analogous helical dipyrromethane-metal complexes containing Mn(II) and Fe(II) have been reported, wherein the dipyrromethane bears a geminal dimethyl group at the meso position [26]. Related to these structures are the "accordion-porphyrins," which contain two bis(imino)dipyrromethanes, each of which is singly metal-coordinated and held apart from the other by α,ω-diaminoalkyl groups spanning the imine moieties [25]. Molecular modeling of $(3a)_2Zn_2$ shows that the zinc-$N_{pyrrole}$ distance (1.95 Å) and the zinc-$N_{imine}$ distance (2.19 Å) match well with those of known pyrrole-imine zinc complexes (1.93 Å and 2.16 Å) [44]. No discernible differences in conformation were observed owing to the nature of the meso substituent (aryl, alkyl, H).

Reactivity of complexes $(3a)_2Zn_2$ and $(5a)_2Zn$. To determine whether complexes $(3a)_2Zn_2$ and $(5a)_2Zn$ were intermediates along the path to porphyrin or unreactive side products, the order-of-addition of reactants was examined. In the standard reaction, an ethanol solution of bis(imino)dipyrromethane 3a and dipyrromethane 1b is treated with Zn(OAc)$_2$, followed by reflux exposed to air for 2 h, whereupon porphyrin is obtained in ~40% yield (Table 7, Entry 1). Three experiments were performed:

(1) A mixture of dipyrromethane 1b was treated with Zn(OAc)$_2$ at room temperature for 30 min before adding bis(imino)dipyrromethane 3a, and then refluxing for 2 h (Entry 2). Porphyrin was obtained in yield comparable to that of the standard reaction (36-39%), indicating stability of the dipyrromethane to the reaction conditions.

(2) Bis(imino)dipyrromethane 3a was treated with Zn(OAc)$_2$ at room temperature for a period (1 to 30 min) prior to the addition of dipyrromethane 1b, and then refluxing for 2 h (Table 7, Entries 3-6). No change in yield from that of the standard reaction was observed, indicating the ability to form porphyrin from the complex $(3a)_2Zn_2$.

(3) A mixture of bis(imino)dipyrromethane 3a and Zn(OAc)$_2$ was refluxed for a period (1 to 30 min) prior to the addition of dipyrromethane 1b, and then refluxing for 2 h (Table 7, Entries 7-11). The yield of porphyrin declined as the former reaction time was extended: 10 min (35%); 30 min (29%); 1 h (23%); 2 h (21%); 24 h (2%). The reflux period converts $(3a)_2Zn_2$ to $(5a)_2Zn$ and high molecular weight material. Thus, bis(dipyrrinato)zinc(II) complex $(5a)_2Zn$ is not an intermediate along the path to porphyrin, whereas $(3a)_2Zn_2$ is a viable precursor to the porphyrin (either by direct reaction with a dipyrromethane or by reversion to 3a).

TABLE 7

Effects on the order of the addition of substrate and reagent in formation of porphyrin Zn4ab[a]

| Entry | 1st step Reagents | Time (temp) | 2nd step Reagents | Time (temp) | Yield (%)[b] |
|---|---|---|---|---|---|
| 1 | 1b + 3a | 30 min (rt) | Zn(OAc)$_2$ | 2 h (reflux) | 40 |
| 2 | 1b + Zn(OAc)$_2$ | 30 min (rt) | 3a | 2 h (reflux) | 40 |
| 3 | 3a + Zn(OAc)$_2$ | 1 min (rt) | 1b | 2 h (reflux) | 36 |
| 4 | | 3 min (rt) | | | 36 |
| 5 | | 10 min (rt) | | | 39 |
| 6 | | 30 min (rt) | | | 38 |
| 7 | 3a + Zn(OAc)$_2$ | 10 min (reflux) | 1b | 2 h (reflux) | 35 |
| 8 | | 30 min (reflux) | | | 29 |
| 9 | | 1 h (reflux) | | | 23 |
| 10 | | 2 h (reflux) | | | 21 |
| 11 | | 24 h (reflux) | | | 2 |

[a]Reaction conditions; [3a]and [1b] = 31.6 mM, Zn(OAc)$_2$ (10 equiv) in EtOH.
[b]The yields of porphyrin were determined using absorption spectroscopy. No scrambling was observed in each reaction (LD-MS analysis).

Reversibility of complex $(3)_2Zn_2$ formation. The reversibility of formation of $(3)_2Zn_2$ was examined via double-labeling crossover (i.e., exchange) experiments (Table 8). Three exchange experiments were performed using samples of $(3a)_2Zn_2$ and $(3j)_2Zn_2$ that were freshly prepared with a stoichiometric amount of Zn(OAc)$_2$. (1) Upon dissolving $(3a)_2Zn_2$ and two mol equiv of 3j in ethanol at room temperature for 20 min, LD-MS analysis showed the molecule ion peak corresponding to each of $(3a)_2Zn_2$, $(3a/3j)Zn_2$, and $(3j)_2Zn_2$, indicating ligand exchange. (2) Analogous treatment of $(3j)_2Zn_2$ and 3a gave a similar result. (3) Upon mixing equimolar quantities of $(3a)_2Zn_2$ and $(3j)_2Zn_2$, again the molecule ion peaks of the two parent complexes and the hybrid complex $(3a/3j)Zn_2$ were observed. These exchange experiments indicate the complexes $(3a)_2Zn_2$ and $(3j)_2Zn_2$ form reversibly and readily undergo ligand exchange. Thus, the failure to form porphyrin from non-aryl substituted bis(imino)dipyrromethanes is not a result of irreversible formation of the corresponding complexes $(3)_2Zn_2$.

TABLE 8

Double-label crossover experiments with complexes $(3)_2Zn_2$[a]

| Entry | Reactants | Products |
|---|---|---|
| 1 | $(3a)_2Zn_2$ + 3j | $(3a)_2Zn_2$, $(3a/3j)Zn_2$, $(3j)_2Zn_2$ |
| 2 | $(3j)_2Zn_2$ + 3a | $(3a)_2Zn_2$, $(3a/3j)Zn_2$, $(3j)_2Zn_2$ |
| 3 | $(3a)_2Zn_2$ + $(3j)_2Zn_2$ | $(3a)_2Zn_2$, $(3a/3j)Zn_2$, $(3j)_2Zn_2$ |

[a]Identified by the presence of the molecule ion peak upon LD-MS analysis.

Conclusion. The condensation of a bis(imino)dipyrromethane+a dipyrromethane proceeds without a Brønsted acid or an added chemical oxidant to give the corresponding zinc-porphyrin. Yields of ~30% are typical, and reactions at concentrations up to 31.6 mM can be employed. A range of meso-substituents can be introduced under reasonably mild conditions, subject to the proviso that an aromatic group is located at the 5-position of the bis(imino)dipyrromethane. The available substituent patterns for trans-AB-porphyrins include aryl/alkyl, aryl/aryl, but not alkyl/alkyl groups; for A-porphyrins the substituent must be aryl (not alkyl). The synthesis of a trans-AB (or A-porphyrin where B=H) can be carried out with the A or B substituent on the dipyrromethane or the bis(imino)dipyrromethane. A difference in yield via the two approaches reflects differences in the condensation process, given that both routes should give the same porphyrinogen. In this context, the failure of reactions with alkyl- or H-substituted bis(imino)dipyrromethanes is believed to result from ineffective condensation rather than oxidation processes. In summary, the routes described herein should broaden the scope of available trans-AB- and A-porphyrins, and can be applied where needed to the synthesis of trans-$A_2$-porphyrins.

Experimental

General. All $^1$H NMR (400 MHz) and $^{13}$C NMR (100 MHz) spectra were obtained in CDCl$_3$ unless noted otherwise. Porphyrins were analyzed by laser desorption mass spectrometry without a matrix (LD-MS) [37]. Fast atom bombardment mass spectrometry (FAB-MS) data are reported for the molecule ion or protonated molecule ion. Absorption spectra were obtained in THF (zinc porphyrins) or CH$_2$Cl$_2$ [bis(imino)dipyrromethane] at room temperature. Column chromatography was performed with flash silica.

Noncommercial compounds. The dipyrromethanes 1a [27], 1b [28], 1c [29], 1d [30], 1e [31], 1f [29], 1g [32], 1h [28], 1i [22], 1j [33], 1k [21], and 1l [1] were prepared using a new method which entails reaction of an aldehyde in 100 equivalents of pyrrole as the solvent containing a Lewis acid (e.g., $InCl_3$) [34].

Spectroscopic yield determination. Yields of porphyrin-forming reactions were determined by removal of aliquots from the reaction mixture followed by absorption spectroscopy of the oxidized product. For example, an ethanol solution of 3a (500 μL, 20.0 mM stock solution, 10.0 μmol of 3a) and an ethanol solution of 1b (500 μL, 20.0 mM stock solution, 10.0 μmol of 1b) were combined and treated with $Zn(OAc)_2$ (18.3 mg, 100 μmol), affording [3a]=[1a]=10 mM. The reaction mixture was refluxed for a designated period. An aliquot (25 μL) of the reaction mixture was removed and diluted with THF (500 μL, 21 times dilution), then 25 μL of this diluted reaction mixture was added to a cuvette containing 3.00 mL of THF (121 times dilution) and the absorption spectrum was recorded (total dilution 2541 times). The yield of the porphyrin was determined by the intensity of the Soret band (412 nm, $\epsilon$=500,000 $M^{-1}$ $cm^{-1}$) measured from the apex to the base of the red edge of the band. In this manner, a Soret band absorption of 1.00 would correspond to a porphyrin yield of 51%.

General Procedures (A) Diformylation and tin complexation, exemplified for dibutyl(1,9-diformyl-5,10-dihydro-5-phenyldipyrrinato)tin (IV) ($Bu_2Sn$-2a). A solution of 1a (2.22 g, 10.0 mmol) in DMF (10.0 mL, 128 mmol) at 0° C. under argon was treated dropwise with $POCl_3$ (1.95 mL, 21.0 mmol). The mixture was stirred for 1 h at room temperature, and then was poured into aqueous NaOH (20 mL of a 20% wt solution). The milky reaction mixture was extracted with $CH_2Cl_2$. The organic extracts were combined, washed with water, dried ($Na_2SO_4$), and filtered. The filtrate was concentrated to dryness. The resulting crude mixture was dissolved in $CH_2Cl_2$ (50 mL), then TEA (4.18 mL, 30.0 mmol) and $Bu_2SnCl_2$ (3.04 g, 10.0 mmol) were added. The mixture was stirred for 30 min at room temperature. The mixture was concentrated to dryness and passed over a pad of silica and eluted with $CH_2Cl_2$ containing 1% TEA. The eluent was concentrated to dryness. The residue was dissolved in a minimum amount of diethyl ether. Then methanol was added, yielding a precipitate, which upon filtration afforded a pink solid (2.96 g, 58%): mp 96-98° C.; $^1$H NMR δ 0.73 (t, J=8.0 Hz, 3H), 0.77 (t, J=8.0 Hz, 3H), 1.13-1.62 (m, 12H), 5.53 (s, 1H), 6.13-6.15 (m, 2H), 7.06 (d, J=4.0 Hz, 2H), 7.12-7.28 (m, 5H) 9.16 (s, 2H); $^{13}$C NMR δ 13.70, 13.76, 24.1, 24.6, 26.2, 26.5, 27.27, 27.32, 45.4, 115.7, 124.1, 127.1, 128.2, 128.9, 138.1, 143.8, 152.2, 178.8. Anal. Calcd for $C_{25}H_{30}N_2O_2Sn$: C, 58.97; H, 5.94; N, 5.50. Found: C, 59.08; H, 5.92; N, 5.50.

(B) Decomplexation of a diformyldipyrromethane-tin complex, exemplified for 1,9-diformyl-5-phenyldipyrromethane (2a). The solution of $Bu_2Sn$-2a (509 mg, 1.00 mmol) in $CH_2Cl_2$ (10 mL) was reacted with TFA (116 μL, 1.50 mmol) for 10 min at room temperature. The solution was concentrated and chromatographed [silica, hexanes/ethyl acetate (1:1)] affording a pale brown solid (220 mg, 79%): mp 159-160° C. (154-156° C. [12]); $^1$H NMR δ 5.58 (s, 1H), 6.06-6.08 (m, 2H), 6.87-6.89 (m, 2H), 7.62-7.38 (m, 5H), 9.18 (s, 2H), 10.59-10.65 (br, 2H); $^{13}$C NMR δ 44.7, 112.0, 122.8, 127.9, 128.7, 129.2, 132.8, 139.4, 142.2, 179.3; Anal. Calcd for $C_{17}H_{14}N_2O_2$: C, 73.37; H, 5.07; N, 10.07. Found: C, 72.77; H, 5.12; N, 9.85; $\lambda_{abs}$ ($CH_2Cl_2$) 303 nm (C) Direct diformylation of a dipyrromethane, exemplified for 1,9-diformyl-5-(pentafluorophenyl)dipyrromethane (2e). A solution of 1e (3.12 g, 10.0 mmol) in DMF (10.0 mL, 128 mmol) at 0° C. under argon was treated dropwise with $POCl_3$ (1.95 mL, 21.0 mmol). The mixture was stirred for 1 h at room temperature, and then was poured into saturated aqueous NaOAc (100 mL). The milky reaction mixture was extracted with $CH_2Cl_2$. The organic extracts were combined, washed with water, dried ($Na_2SO_4$), and filtered. Removal of the solvent and chromatography [silica, ethyl acetate/$CH_2Cl_2$ (1:3)] afforded a brown solid (3.14 g, 85%): mp 180-182° C.; $^1$H NMR δ 6.06 (s, 1H), 6.12-6.14 (m, 2H), 6.88-6.90 (m, 2H), 9.21 (s, 2H), 10.94 (br, 2H); $^{13}$C NMR δ 33.4, 111.5, 122.5, 133.0, 137.6.0, 179.3. Anal. Calcd for $C_{17}H_9F_5N_2O_2$: C, 55.45; H, 2.46; N, 7.61. Found: C, 55.47; H, 2.45; N, 7.66.

(D) Imination of a 1,9-diformyldipyrromethane, exemplified for 1,9-bis[(propylimino)methyl]-5-phenyldipyrromethane (3a). A solution of 2a (83.5 mg, 0.300 mmol) and n-propylamine (500 μL, 6.08 mmol) in THF (1 mL) was stirred at room temperature for 1 h. Removal of the solvent and excess n-propylamine gave a purple solid (102 mg, quantitative): mp 101-105° C.; $^1$H NMR δ 0.88 (t, J=7.2 Hz, 6H), 1.52-1.62 (m, 4H), 3.37 (t, J=7.2 Hz, 4H), 5.42 (s, 1H), 5.87-5.88 (m, 2H), 6.32-6.34 (m, 2H), 7.17-7.32 (m, 5H), 7.86 (s, 2H), 8.31-8.68 (br, 2H); $^{13}$C NMR δ 12.0, 24.5, 44.6, 62.7, 109.5, 114.8, 127.3, 128.7, 128.9, 130.3, 136.8, 141.2, 151.6; FAB-MS obsd 361.2385; calcd 361.2392 [(M+H)$^+$, M=$C_{23}H_{28}N_4$]; $\lambda_{abs}$ ($CH_2Cl_2$) 286 nm.

(E) Imination of a 1,9-diformyldipyrromethane-tin complex, exemplified for 1,9-Bis[(propylimino)methyl]-5-phenyldipyrromethane (3a): A mixture of $Bu_2Sn$-2a (50.0 mg, 98.2 μmol) and n-propylamine (0.161 mL, 1.96 mmol) was stirred for 2 h at room temperature. The excess n-propylamine was evaporated to give the title compound as a pink oil (34.0 mg, quantitative) with satisfactory characterization data.

(F) Porphyrin formation, exemplified for Zn(II)-5-(4-methylphenyl)-15-phenylporphyrin (Zn4ab). A solution of 3a [prepared from 2a (83.5 mg, 0.300 mmol) in situ] and 5-(p-tolyl)dipyrromethane (1b, 70.8 mg, 0.300 mmol) in ethanol (30 mL) was treated with $Zn(OAc)_2$ (550 mg, 3.00 mmol) under reflux for 18 h. The solvent was removed in vacuo, affording a dark purple residue. TLC analysis [silica, hexanes/$CH_2Cl_2$ (1:2)] showed the porphyrin as the sole mobile species, and dark byproducts at the origin. Chromatography of the residue over a short pad of silica [hexanes/$CH_2Cl_2$ (1:2)] afforded a purple solid (60.0 mg, 37%): $^1$H NMR δ 2.75 (s, 2H), 7.58-7.62 (m, 2H), 7.77-7.83 (m, 2H), 8.13-8.18 (m, 2H), 8.26-8.29 (m, 2H), 9.11-9.15 (m, 2H), 9.15-9.19 (m, 2H), 9.41-9.47 (m, 2H), 10.31 (s, 2H); $^{13}$C NMR δ 21.7, 106.6, 120.3, 120.6, 127.4, 128.1, 128.2, 132.2, 132.3, 132.7, 132.9, 135.68, 135.78, 137.8, 141.6, 144.6, 150.61, 150.64, 151.0, 151.2; LD-MS obsd 538.5; FAB-MS obsd 538.1150, calcd 538.1136 ($C_{33}H_{22}N_4Zn$); $\lambda_{abs}$ (THF) 413, 539, 573 nm.

(G) Chromatography-free isolation procedure. The ability to isolate the trans-AB-porphyrin without resort to chromatography is attractive for scale-up purposes. The synthesis of a trans-AB-porphyrin (Zn4ab) was performed in the standard manner using 1.0 mmol of reactants. After reflux for 18 h, the crude reaction mixture was concentrated to dryness. The residue was washed with diethyl ether and filtered to remove the excess zinc acetate and pyrrolic polymer byproducts. The filtrate was concentrated to dryness. The residue was washed with diethyl ether and the sparingly soluble polymer byproducts were removed by filtration. The filtrate was concentrated. The procedure was repeated ten times. The resulting crude porphyrin was recrystallized from $CH_2Cl_2$/cyclohexane affording pure porphyrin Zn4ab (105 mg, 31%). The absence of an added chemical oxidant greatly facilitated purification.

Synthesis.

Dibutyl(1,9-diformyl-5,10-dihydro-5-mesityldipyrrinato) tin(IV) ($Bu_2Sn$-2c). Following procedure A with slight modification (formylation was carried out at 80° C. instead of room temperature, NaOAc was used instead of NaOH), reaction of 10.0 mmol of 1c afforded a pink solid (3.69 g, 67%): mp 137-139° C.; $^1$H NMR δ 0.75 (t, J=8.0 Hz, 3H), 0.81 (t, J=8.0 Hz, 3H), 1.18-1.65 (m, 15H), 2.30 (s, 3H), 2.48 (s, 3H), 5.80-5.82(m,2H), 5.83 (s, 1H), 6.78 (s, 1H), 6.97 (s, 1H), 7.03 (d, J=4.0 Hz, 2H), 9.13 (s, 2H); $^{13}$C NMR δ 13.75, 13.77, 20.2, 20.91, 21.14, 23.6, 24.8, 26.47, 26.68, 27.51, 27.58, 39.7, 114.5, 124.3, 129.0, 130.9, 136.01, 136.13, 136.8, 137.7, 138.1, 152.7, 178.2. Anal. Calcd for $C_{28}H_{36}N_2O_2Sn$: C, 61.00; H, 6.58; N, 5.08. Found: C, 61.16; H, 6.63; N. 4.93.

Dibutyl[1,9-diformyl-5,10-dihydro-5-(4-methoxyphenyl) dipyrrinato]tin(IV) (Bu$_2$Sn-2d). Following procedure A, reaction of 5.00 mmol of 1d afforded a pink solid (1.43 g, 53%): mp 90-92° C.; $^1$H NMR δ 0.73 (t, J=8.0 Hz, 3H,), 0.77 (t, J=8.0 Hz, 3H), 1.14-1.58 (m, 12H), 3.76 (s, 3H), 5.47 (s, 1H), 6.13 (d, J=4.0 Hz, 2H), 6.80 (d, J=8.0 Hz, 2H), 7.03-7.06 (m, 4H), 9.15 (s, 2H); $^{13}$C NMR δ 13.71, 13.76, 24.1, 24.5, 27.27, 27.30, 44.6, 55.4, 114.3, 115.6, 124.1, 129.3, 135.9, 138.1, 152.7, 158.6, 178.7. Anal. Calcd for $C_{26}H_{32}N_2O_3Sn$: C, 57.91; H, 5.98; N, 5.19. Found: C, 57.94; H, 5.96; N, 5.18.

1,9-Diformyl-5-(4-methoxyphenyl)dipyrromethane (2d). Following procedure B, reaction of 1.00 mmol of Bu$_2$Sn-2d afforded a white solid (253 mg, 82%): mp 193-195° C. (197-199° C. [14]); $^1$H NMR δ 3.81 (s, 3H), 5.51 (s, 1H), 6.06-6.08 (m, 2H), 6.87-6.89 (m, 4H), 7.16-7.18 (m, 2H), 9.25 (s, 2H), 10.07-10.15 (br, 2H); $^{13}$C NMR δ 43.8, 55.5, 111.6, 114.7, 122.3, 129.7, 131.2, 132.8, 141.7, 159.3, 179.1. Anal. Calcd for $C_{18}H_{16}N_2O_3$: C, 70.12; H, 5.23; N, 9.09. Found: C, 70.18; H, 5.28; N, 8.94.

Dibutyl[1,9-diformyl-5,10-dihydro-5-(4-iodophenyl) dipyrrinato]tin(IV) (Bu$_2$Sn-2f). Following procedure A, reaction of 10.0 mmol of 1f afforded a dark pink solid (2.92 g, 46%): mp 130-132° C.; $^1$H NMR δ 0.72 (t, J=8.0 Hz, 3H), 0.78 (t, J=8.0 Hz, 3H), 1.12-1.58 (m, 12H), 5.47 (s, 1H), 6.13 (d, J=4.0 Hz, 2H), 6.87 (d, J=8.0 Hz, 2H), 7.06 (d, J=4.0 Hz, 2H), 7.58 (d, J=8.0 Hz, 2H), 9.17 (s, 2H); $^{13}$C NMR δ 13.66, 13.76, 24.1, 24.7, 26.2, 26.5, 27.22, 27.34, 44.9, 92.5, 115.6, 124.1, 130.2, 138.2, 143.5, 151.3, 179.0. Anal. Calcd for $C_{25}H_{30}N_2O_2Sn$: C, 47.28; H. 4.60; N, 4.41. Found: C, 47.49; H, 4.68; N, 4.35.

1,9-Diformyl-5-(4-iodophenyl)dipyrromethane (2f). Following procedure B. reaction of 1.00 mmol of Bu$_2$Sn-2f afforded a brown solid (348 mg, 86%): mp 170-172° C.; $^1$H NMR δ 5.53 (s, 1H), 6.06-6.08 (m, 2H), 6.91-6.93 (m, 2H), 7.01-7.05 (m, 2H), 7.65-7.69 (m, 2H), 9.16 (s, 2H), 10.59-10.67 (br, 2H); $^{13}$C NMR δ 44.3, 93.6, 112.0, 122.4, 130.7, 138.3, 139.2, 141.0, 179.3. Anal. Calcd for $C_{17}H_{13}N_2O_2$: C, 50.51; H, 3.24; N, 6.93. Found: C, 50.48; H, 3.16; N, 6.87.

1,9-Diformyl-5-methyldipyrromethane (2g). Following procedure C with slight modification (NaOH was used instead of NaOAc), reaction of 2.00 mmol of 1 g afforded a pale yellow solid (337 mg, 78%): mp 151-153° C.; $^1$H NMR δ 1.75 (d, J=7.3 Hz, 3H), 4.38 (q, J=7.3, 14.6 Hz, 1H), 6.20-6.23 (m, 2H), 6.92-6.95 (m, 2H), 9.42 (s, 2H), 10.89-11.18 (br, 2H); $^{13}$C NMR δ 19.0, 32.6, 109.1, 123.4, 132.8, 144.2, 179.6. Anal. Calcd for $C_{12}H_{12}N_2O_2$: C, 66.65; H, 5.59; N, 12.96. Found: C, 66.53; H, 5.67; N. 13.02.

Dibutyl(1,9-diformyl-5,10-dihydro-5-n-pentyldipyrrinato)tin(IV) (Bu$_2$Sn-2h). Following procedure A, reaction of 10.0 mmol of 1 h afforded a brown viscous liquid (2.11 g, 42%): $^1$H NMR δ 0.64-1.82 (m, 29H), 4.35 (t, J=6.0 Hz, 1H), 6.33 (d, J=3.6 Hz, 2H), 7.10 (d, J=3.6 Hz, 2H), 9.13 (s, 2H); $^{13}$C NMR δ 13.64, 13.78, 14.21, 14.35, 22.6, 22.8, 23.4, 25.2, 26.1, 26.3, 26.7, 27.1, 27.3, 27.5, 31.82, 31.84, 39.2, 41.7, 114.5, 124.1, 138.1, 153.5, 178.3; FAB-MS obsd 505.1850, calcd 505.1877 [(M+H)$^+$, M=$C_{24}H_{36}N_2O_2Sn$].

1,9-Diformyl-5-n-pentyldipyrromethane (2h). Following procedure B, reaction of 1.00 mmol of Bu$_2$Sn-2h afforded a brown viscous liquid (196 mg, 72%): $^1$H NMR δ 0.85, (t, J=7.6 Hz, 3H), 1.27-1.30 (m, 6H), 2.13-2.15 (m, 2H), 4.19 (t, J=7.6 Hz, 1H), 6.21-6.23 (m, 2H), 6.96-6.98 (m, 2H), 9.41 (s, 2H), 11.22 (br, 2H); $^{13}$C NMR δ 14.2, 22.6, 27.5, 31.6, 33.5, 38.8, 110.0, 124.0, 132.7, 143.6, 179.6; FAB-MS obsd 273.1577, calcd 273.1603 [(M+H)$^+$, M=$C_{16}H_{20}N_2O_2$].

Alternatively, following procedure C with slight modification (NaOH was used instead of NaOAc), reaction of 3.00 mmol of 1 h afforded a brown viscous liquid (588 mg, 72%) with satisfactory characterization data.

1,9-Diformyl-5-(tridec-7-yl)dipyrromethane (2i). Following procedure C with slight modification (NaOH was used instead of NaOAc), reaction of 1.00 mmol of 1i afforded a pale yellow solid (179 mg, 47%): mp 86-88° C.; $^1$H NMR δ 0.83 (t, J=7.1 Hz, 6H), 1.09-1.32 (m, 20H), 2.33-2.40 (m, 1H), 4.09 (d, J=10.7 Hz, 1H), 6.17-6.21 (m, 2H), 6.92-6.96 (m, 2H), 9.45 (s, 2H), 11.16-11.32 (br, 2H); $^{13}$C NMR δ 14.3, 22.8, 25.6, 29.6, 30.6, 31.9, 40.8, 43.5, 111.4, 123.7, 133.1, 142.9, 179.5; Anal. Calcd for $C_{24}H_{36}N_2O_2$: C, 74.96; H, 9.44; N, 7.28. Found: C, 74.82; H, 9.47; N, 7.27.

1,9-Diformyldipyrromethane (2j). Following procedure C with slight modification (formylation was carried out at 80° C. instead of room temperature), reaction of 10.0 mmol of 1j afforded a pale yellow solid (707 mg, 70%): mp 227-229° C. (229-231° C. [37]); $^1$H NMR (THF-d$_8$) δ 3.13-3.17 (m, 2H), 5.54-5.57 (m, 2H), 6.33-6.36 (m, 2H), 8.93 (s, 1H), 10.64-10.97 (br, 2H); $^{13}$C NMR (THF-d$_8$) δ 26.3, 109.4, 120.6, 133.5, 137.8, 177.6; FAB-MS obsd 203.0807, calcd 203.0821 [(M+H)$^+$, M=$C_{11}H_{10}N_2O_2$].

1,9-Bis[(phenylimino)methyl]dipyrromethane (3a-Ph). A solution of 2a (278 mg, 1.00 mmol) and aniline (182 μL, 2.00 mmol) in CH$_2$Cl$_2$ (6.7 mL) was treated with TFA (154 μL, 2.00 mmol) at room temperature for 30 min. Triethylamine (418 μL, 3.00 mmol) was added and the reaction mixture was concentrated to dryness. Column chromatography [silica, hexanes/ethyl acetate/TEA (66:33:1)] afforded a pale purple solid (330 mg, 77%): mp 138-141° C.; $^1$H NMR δ 5.06-5.21 (m, 1H), 6.52-6.56 (m, 2H), 6.74-6.92 (m, 2H), 7.07-7.47 (m, 15H), 8.13 (s, 2H), 9.84-10.78 (br, 2H); $^{13}$C NMR δ 44.5, 110.4, 117.3, 121.3, 125.6, 127.0, 128.5, 128.7, 129.3, 131.1, 138.5, 140.7, 149.6, 151.3. Anal. Calcd for $C_{29}H_{29}N_4$: C, 81.28; H, 5.65; N, 13.07. Found: C, 81.31; H, 5.74; N, 13.02.

1,9-Bis[(p-anisylimino)methyl]dipyrromethane (3a-An). A solution of 2a (278 mg, 1.00 mmol) and p-anisidine (246 mg, 2.00 mmol) in CH$_2$Cl$_2$ (6.7 mL) was treated with TFA (154 μL, 2.00 mmol) at room temperature for 30 min. Triethylamine (558 μL, 4.00 mmol) was added and the reaction mixture was concentrated to dryness. Column chromatography [silica, hexanes/ethyl acetate/TEA (66:33:1)] afforded a pale purple solid (338 mg, 69%): mp 85-87° C.; $^1$H NMR δ 3.81 (s, 6H), 5.17-5.20 (m, 1H), 5.79-5.82 (m, 2H), 6.48-6.52 (m, 2H), 6.83-6.88 (m, 4H), 6.89-6.95 (m, 2H), 7.10-7.14 (m, 2H), 7.15-7.19 (m, 2H), 8.11 (s, 2H); $^{13}$C NMR δ 44.1, 55.5, 109.9, 114.3, 116.4, 122.1, 126.5, 128.19, 128.26, 131.07, 138.2, 140.8, 144.1, 147.8, 157.6; FAB-MS obsd 489.2291, calcd 489.2289 [(M+H)$^+$, M=$C_{31}H_{28}N_4O_2$].

1,9-Bis[(benzylimino)methyl]dipyrromethane (3a-Bz). A solution of 2a (139 mg, 0.500 mmol) and benzylamine (109 μL, 1.00 mmol) in THF (1 mL) was stirred at room temperature for 2 h. Removal of the solvent gave a purple solid (210 mg, quantitative, estimated 95% pure by $^1$H NMR spectroscopy): $^1$H NMR δ 4.65 (s, 4H), 5.38 (s, 1H), 5.91-5.93 (m, 2H), 6.40-5.42 (m, 2H), 7.16-7.35 (m, 15H), 8.04 (s, 2H); $^{13}$C NMR δ 44.4, 64.3, 109.6, 115.9, 127.04, 127.16, 128.2, 128.5, 128.7, 137.5, 139.4, 152.9 (three carbons corresponding to the phenyl unit are missing due to overlap); FAB-MS obsd 457.2385, calcd 457.2385 [(M+H)$^+$, M=$C_{31}H_{28}N_4$].

Zn(II)-5-(4-Methylphenyl)-15-phenylporphyrin (Zn4ab). Following procedure F, reaction of 0.300 mmol of 2a and 1b afforded a purple solid (10.0 mg, 6%) of Zn4ab with satisfactory characterization data.

Zn(II)-5-(4-Methoxyphenyl)-15-(pentafluorophenyl)porphyrin (Zn4de). Following procedure F, reaction of 0.300 mmol of 3d (prepared from 2d in situ) and 1e afforded a purple solid (58 mg, 30%): $^1$H NMR δ 4.14 (s, 3H), 7.34 (d, J=8.0 Hz, 2H), 8.17 (d, J=8.0 Hz, 2H), 9.05 (d, J=4.0 Hz, 2H), 9.20 (d, J=4.0 Hz, 2H), 9.45 (d, J=4.0 Hz, 2H), 9.53 (d, J=4.0 Hz, 2H), 10.36 (s, 2H); $^{13}$C NMR (THF-d$_8$) δ 55.9, 99.9, 107.2, 113.0, 122.3, 130.8, 132.4, 133.5, 133.9, 136.3, 136.7, 150.6, 150.8, 151.1, 151.4, 160.8; LD-MS obsd 644.4; FAB-MS obsd 644.0645, calcd 644.0614 ($C_{33}H_{17}F_5N_4OZn$); $\lambda_{abs}$ (THF) 413, 539, 574 nm. Alternatively, reaction of 0.500 mmol of 3e (prepared from 2e in situ) and 1d afforded a purple solid (103 mg, 32%) of Zn4de with satisfactory analytical data.

Zn(II)-5-Ethoxycarbonyl-15-(4-iodophenyl)porphyrin (Zn4fk). Following procedure F, reaction of 0.500 mmol of 3f (prepared from 2f in situ) and 1k afforded a purple solid (124 mg, 38%): $^1$H NMR δ 1.82 (t, J=8.0 Hz, 3H), 5.08 (q, J=8.0 Hz, 2H), 8.01 (d, J=8.0 Hz, 2H), 8.17 (d, J=8.0 Hz, 2H), 9.04 (d, J=4.0 Hz, 2H), 9.42 (d, J=4.0 Hz, 2H), 9.50 (d, J=4.0 Hz, 2H), 9.67 (d, J=4.0 Hz, 2H), 10.32 (s, 2H); $^{13}$C NMR (THF-d$_8$) δ 15.4, 63.2, 94.6, 107.4, 109.6, 121.2, 132.3, 132.5, 133.0, 133.6, 136.7, 137.4, 143.9, 150.10, 150.12, 150.21, 150.86, 150.88, 151.1, 172.6; LD-MS obsd 646.2; FAB-MS obsd 646.9932, calcd 646.9922 ($C_{29}H_{19}IN_4O_2Zn$); $\lambda_{abs}$ (THF) 412, 538, 574 nm.

Zn(II)-5,15-Diphenylporphyrin (Zn4aa). Following procedure F, reaction of 0.500 mmol of 3a (prepared from 2a in situ) and 1a afforded a purple solid (94.6 mg, 36%): $^1$H NMR (THF-d$_8$) δ 7.78-7.80 (m, 6H), 8.24-8.27 (m, 4H), 9.03 (d, J=4.0 Hz, 4H), 9.41 (d, J=4.0 Hz, 4H), 10.28 (s, 2H); $^{13}$C NMR (THF-d$_8$) δ 106.6, 120.4, 127.4, 128.2, 132.4, 132.8, 135.8, 144.6, 150.6, 151.0; LD-MS obsd 523.5; FAB-MS obsd 524.1007, calcd 524.0979 ($C_{32}H_{20}N_4Zn$); $\lambda_{abs}$ (THF) 412, 538, 573 nm.

Zn(II)-5-Mesitylporphyrin (Zn4cj). Following procedure F, reaction of 0.500 mmol of 3c (prepared from Bu$_2$Sn-2c in situ) and 1j afforded a purple solid (93.5 mg, 38%): $^1$H NMR (THF-d$_8$) δ 1.82 (s, 6H), 2.65 (s, 3H), 7.34 (s, 2H), 8.87 (d, J=4.0 Hz, 2H), 9.38 (d, J=4.0 Hz, 2H), 9.50 (s, 4H), 10.25 (s, 2H), 10.26 (s, 1H); $^{13}$C NMR (THF-d$_8$) δ 21.7, 22.2, 104.9, 105.6, 118.5, 128.6, 131.3, 132.68, 132.81, 138.2, 140.1, 140.8, 150.2, 150.54, 150.63, 151.0; LD-MS obsd 489.6; FAB-MS obsd 490.1146, calcd 490.1136 ($C_{29}H_{22}N_4Zn$); $\lambda_{abs}$ (THF) 406, 532, 566 nm. Attempts to carry out the reaction of 0.250 mmol of 3j (prepared from 2j in situ) and 1c did not affored the desired porphyrin.

Zn(II)-5-n-Pentyl-15-phenylporphyrin (Zn4ah). Following procedure F, reaction of 0.100 mmol of 3a (prepared from 2a in situ) and 1h afforded a purple solid (16.6 mg, 32%): $^1$H NMR δ 1.00 (t, J=7.2 Hz, 3H), 1.57-1.62 (m, 2H), 1.86-1.89 (m, 2H), 2.61-2.64 (m, 2H), 5.20 (t, J=8.0 Hz, 3H), 7.75-7.77 (m, 3H), 8.20-8.23 (m, 2H), 8.96 (d, J=4.0 Hz, 2H), 9.34 (d, J=4.0 Hz, 2H), 9.45 (d, J=4.0 Hz, 2H), 9.76 (d, J=4.0 Hz, 2H), 10.18 (s, 1H); $^{13}$C NMR δ 14.7, 23.9, 33.9, 36.4, 40.2, 106.1, 120.7, 127.4, 128.1, 130.0, 132.3, 132.52, 132.64, 135.7, 144.7, 150.17, 150.29, 151.11, 151.18; LD-MS obsd 517.8; FAB-MS obsd 518.1458, calcd 518.1449 [(M+H)$^+$, M=$C_{29}H_{22}N_4Zn$]; $\lambda_{abs}$ (THF) 412, 540, 574 nm. Attempts to carry out the reaction of 0.25 mmol of 3h (prepared from 2h in situ) and 1a did not affored the desired porphyrin.

Studies Probing the Reaction Course.

Stability of bis(imino)dipyrromethanes. A 1,9-diformyl-dipyrromethane typically affords a pale yellow solution in ethanol. Treatment with n-propylamine affords the bis(imino)dipyrromethane 3 as a pale orange solution, and upon isolation, a pale orange solid. On standing, the solution (or solid) turns purple over the course of a few hours (or days). The $^1$H NMR spectrum showed diminution of the resonances corresponding to 3a and growth of resonances associated with the dipyrrin 5a. The singlet (5.42 ppm) corresponding to the 5-position of the dipyrromethane had vanished, the singlet corresponding to the imine proton shifted from 7.86 ppm to 8.32 ppm, and two multiplets corresponding to the β-pyrrolic protons shifted from 5.87 ppm and 6.33 ppm to 6.62 and 6.80 ppm, respectively. The absorption spectrum of the mixture showed a strong absorption at 481 nm, as expected for the dipyrrin framework [43]. Attempts to analyze the reaction mixture by TLC were not fruitful owing to the very high polarity of the starting bis(imino)dipyrromethane 3a. Note that the conversion of 3a→5a may be quite limited yet the solution appears deeply colored. By contrast, the bis(imino)dipyrromethanes bearing an alkyl substituent or no substituent (e.g., 3j) were resistant to oxidation; thus, the formation of the corresponding bis(imino)dipyrrin (e.g., 5j) was not observed at room temperature over the course of 24 h.

Observation of complexes (3)$_2$Zn$_2$ during porphyrin-forming reactions. In general, the treatment of a bis(imino)dipyrromethane with Zn(OAc)$_2$ in the absence of a dipyrromethane afforded the zinc complex, regardless of the nature of the meso substituent. During attempted porphyrin formation in the presence of a dipyrromethane, however, the observation of complex (3)$_2$Zn$_2$ depends on both the concentration of the reaction and the nature of the substituent. (1) Concentration: LD-MS analysis of a sample from the crude reaction mixture performed at 10 or 31.6 mM typically gave the peak expected for the zinc porphyrin (m/z=538.5 for Zn4ab. derived from 3a+1b) with the absence of any peak due to (3a)$_2$Zn$_2$. When reaction was carried out at higher concentration (100 or 316 mM, instead of 10 or 31.6 mM), the expected molecule ion peak of the porphyrin was typically accompanied by the peak at m/z=844.0 due to (3a)$_2$Zn$_2$. (2) Substituents: For aryl-substituted bis(imino)dipyrromethanes, the reactions at 10.0 or 31.6 mM proceeded well and no complex was observed. However, the reactions of bis(imino)dipyrromethane 3j or 5-alkyl substituted bis(imino)dipyrromethane 3l proceeded poorly, and the peak (m/z=692.3 for 3j, 832.6 for 3l) corresponding to the complex analogous to (3a)$_2$Zn$_2$ was observed. The complex (3j)$_2$Zn$_2$ forms reversibly (vide infra); thus, the formation of the complexes does not appear to be the source of the failure to form the corresponding porphyrin.

Isolation of (3a)$_2$Zn$_2$. A solution of 3a (200 μmol, prepared from 2a in situ) in ethanol (10 mL) was treated with Zn(OAc)$_2$ (36.6 mg, 100 μmol) for 10 min. The reaction mixture was concentrated to dryness, affording (3a)$_2$Zn$_2$ quantitatively: $^1$H NMR δ 1.12 (t, J=7.2 Hz, 12H), 1.71-1.85 (m, 8H), 3.37-3.47 (m, 8H), 5.55-5.59 (m, 2H), 6.24-6.28 (m, 4H), 6.94-6.99 (m, 4H), 7.20-7.38 (m, 14H); $\lambda_{abs}$ (CH$_2$Cl$_2$) 333 nm; FAB-MS obsd 845.2923; calcd 845.2976 [(M+H)$^+$, M=$C_{46}H_{52}N_8Zn_2$]. Prolonged examination of the sample by FAB-MS (3-nitrobenzyl alcohol matrix) resulted in alteration of the pattern of peaks in the molecule-ion region. Electron-impact mass spectrometry as well as LD-MS analysis (without a matrix) afforded a rich isotopic distribution in close agreement with expectation owing to the presence of two zinc atoms. Attempts to chromatograph or obtain crystals of (3a)$_2$Zn$_2$ (also for (3j)$_2$Zn$_2$ and (3l)$_2$Zn$_2$) were to no avail. The failure to obtain crystals may stem from several factors, including the presence of stereoisomers, susceptibility to oxidation, and relatively weak complexes.

Demetalation of $(3a)_2Zn_2$. A solution of $(3a)_2Zn_2$ (100 μmol, prepared from 3a in situ) in $CH_2Cl_2$ (10 mL) was washed with water (10 mL). The organic phase was dried and concentrated to dryness. $^1H$ NMR spectroscopy of the residue showed demetalation of $(3a)_2Zn_2$ to 3a (>60%), together with the formation of unknown species.

Isolation of bis(dipyrrinato)Zn(II) complex [$(5a)_2Zn$]. A solution of $(3a)_2Zn_2$ (200 μmol, prepared from 3a in situ) in ethanol (10 mL) was refluxed for 2 days. The reaction mixture was concentrated to dryness. The residue was precipitated with $CH_2Cl_2$/hexanes and filtered to remove the excess pyrrolic polymer byproducts. The filtrate was concentrated to dryness. The residue was washed with hexanes, sonicated, and filtered. The filtrate was concentrated. The procedure was repeated ~10 times, affording a purple solid (24.8 mg, estimated >85% purity by $^1H$ NMR spectroscopy): $^8H$ NMR δ 0.62-0.66 (m, 12H), 1.19-1.26 (m, 8H), 3.11-3.16 (m, 8H), 6.67-6.71 (m, 8H), 7.24-7.53 (m, 10H), 7.99 (s, 1H); LD-MS obsd 778.4; FAB-MS obsd 779.3495; calcd 779.3528 [(M+H)$^+$, M=$C_{46}H_{52}N_8Zn$]; $\lambda_{abs}$ ($CH_2Cl_2$) 545 nm.

Exchange reactions. (A) $(3a)_2Zn_2+(3j)_2Zn_2$. An ethanol solution of $(3a)_2Zn_2$ (500 μL, 10.0 mM stock solution freshly prepared from 10.0 μmol of 3a, containing 5.00 μmol of $(3a)_2Zn_2$) and an ethanol solution of $(3j)_2Zn_2$ (500 μL, 10.0 mM stock solution freshly prepared from 10.0 μmol of 3j, containing 5.00 μmol of $(3j)_2Zn_2$) were combined, affording [$(3a)_2Zn_2$]=[$(3j)_2Zn_2$]=5.00 mM. The reaction mixture was stirred at room temperature for 20 min, and a sample was subjected to LD-MS analysis. LD-MS obsd 692.3, 768.4, 844.4; calcd 692.2 [$(3j)_2Zn_2$, M=$C_{46}H_{52}N_8Zn_2$], 768.3 [(3a)(3j)Zn$_2$, M=$C_{46}H_{52}N_8Zn_2$], 844.3 [$(3a)_2Zn_2$, M=$C_{46}H_{52}N_8Zn_2$].

(B) $(3a)_2Zn_2+3j$. An ethanol solution of $(3a)_2Zn_2$ (500 μL, 10.0 mM stock solution freshly prepared from 10.0 μmol of 3a, containing 5.00 μmol of $(3a)_2Zn_2$) and an ethanol solution of 3j (500 μL, 20.0 mM stock solution, 10.0 μmol of 3a) were combined, affording [$(3a)_2Zn_2$]=5.00 mM, [3j]=10.0 mM. The reaction mixture was stirred at room temperature for 10 min, and a sample was subjected to LD-MS analysis. LD-MS obsd 692.0, 768.1, 844.1.

(C) $3a+(3j)_2Zn_2$. An ethanol solution of $(3j)_2Zn_2$ (500 μL, 10.0 mM stock solution freshly prepared from 10.0 μmol of 3j, containing 5.00 μmol of $(3j)_2Zn_2$) and an ethanol solution of 3a (500 μL, 20.0 mM stock solution, 10.0 μmol of 3a) were combined, affording [$(3a)_2Zn_2$]=5.00 mM, [3j]=10.0 mM. The reaction mixture was stirred at room temperature for 10 min, and a sample was subjected to LD-MS analysis: LD-MS obsd 692.2, 768.2, 844.2.

REFERENCES

1. Rao P D, Dhanalekshmi S, Littler B J, Lindsey J S. *J. Org. Chem.* 2000; 65: 7323-7344.
2. Setsune Ji, *J. Porphyrins Phthalocyanines* 2004; 8: 93-102.
3. a) Senge M O, Feng X. *Tetrahedron Lett.* 1999; 40: 4165-4168. b) Senge M O, Feng X. *J. Chem Soc. Perkin Trans. 1* 2000; 3615-3621. c) Feng X, Senge M O. *J. Chem. Soc. Perkin Trans. 1* 2001; 1030-1038. d) Senge M O, Bischoff I. *Eur. J. Org. Chem.* 2001; 1735-1751. e) Hartnell R D, Edwards A J, Arnold D P. *J. Porphyrins Phthalocyanines* 2002; 6: 695-707.
4. a) Osuka A, Liu Bl, Maruyama K. *J. Org. Chem.* 1993; 58: 3582-3585. b) Lee D A, Smith K M. *J. Chem. Soc. Perkin Trans. 1* 1997; 1215-1228. c) Hombrecher H K, Horter G. *Liebigs Ann. Chem.* 1991; 219-227. d) Schell C, Hombrecher H K. *Bioorg. Med. Chem.* 1999; 7: 1857-1865.
5. a) Choi M S, Aida T, Yamazaki T, Yamazaki I. *Angew. Chem. Int. Ed. Engl.* 2001; 40: 3194-3198. b) Aratani N, Cho H S, Ahn T K, Cho S, Kim D, Sumi H, Osuka A. *J. Am. Chem. Soc.* 2003; 125: 9668-9681.
6. Sutton J M, Clarke O J, Fernandez N, Boyle R W. *Bioconjugate Chem.* 2002; 13: 249-263.
7. Ema T, Kuroda Y, Ogoshi H. *Tetrahedron Lett.* 1991; 32: 4529-4532.
8. Clarke O J, Boyle R W. *Tetrahedron Lett.* 1998; 39: 7167-7168.
9. Geier G R III, Callinan J B, Rao P D, Lindsey J S. *J. Porphyrins Phthalocyanines* 2001; 5: 810-823.
10. Fan D, Taniguchi M, Yao Z, Dhanalekshmi S, Lindsey J S. *Tetrahedron* 2005; submitted.
11. a) Manka J S, Lawrence D S. *Tetrahedron Lett.* 1989; 30: 6989-6992. b) Lecas-Nawrocka A, Boitrel B, Rose E. *Tetrahedron Lett.* 1992; 33: 481-484. c) Wytko J, Berl V, McLanghlin M, Tykwinski R R, Schreiber M, Diederich F, Boudon C, Gisselbrecht J P, Gross M. *Helv. Chim. Acta* 1998; 81: 1964-1977. d) Odobel F. Suresh S, Blart E, Nicolas Y, Quintard J P, Janvier P, Le Questel J Y, Illien B, Rondeau D, Richomme P, Haupl T, Wallin S, Hammarström L. *Chem. Eur. J.* 2002; 8: 3027-3046.
12. Brückner C, Posakony J J, Johnson C K, Boyle R W, James B R, Dolphin D. *J. Porphyrins Phtlhalocyanines* 1998; 2: 455-465.
13. Khoury R G, Jaquinod L, Aoyagi K, Olmstead M M, Fisher A J, Smith K M. *Angew. Chem. Int. Ed. Engl.* 1997; 36: 2497-2500.
14. Wickramasinghe A, Jaquinod L, Nurco D J, Smith K M. *Tetrahedron* 2001; 57: 4261-4269.
15. Tanaka T. Endo K, Aoyama Y. *Bull. Chem. Soc. Jpn.* 2001; 74: 907-916.
16. Harris D, Johnson A W, Gaete-Holmes R. *Bioorg. Chem.* 1980; 9: 63-70.
17. Wiehe A, Ryppa C, Senge M O. *Org. Lett.* 2002; 4: 3807-3809.
18. Nudy L R, Hutchinson H G, Schieber C, Longo F R. *Tetrahedron* 1984; 40: 2359-2363.
19. Hatscher S, Senge M O. *Tetrahedron Lett.* 2003; 44: 157-160.
20. Gunter M J, Mander L N. *J. Org. Chem.* 1981; 46: 4792-4795.
21. Trova M P, Gauuan P J F, Pechulis A D, Bubb S M, Bocckino S B, Crapo J D, Day B J. *Bioorg. Med. Chem.* 2003; 11: 2695-2707.
22. Thamyongkit P, Speckbacher M, Diers J R, Kee H L, Kirmaier C, Holten D, Bocian D F, Lindsey J S. *J. Org. Chem.* 2004; 69: 3700-3710.
23. Tabushi I, Sakai Ki, Yamamura K. *Tetrahedron Lett.* 1978; 19: 1821-1824.
24. a) Beer P D, Cheetham A G, Drew M G B, Fox O D, Hayes E J, Rolls T D. *Dalton Trans.* 2003; 603-611. b) Love J B, Blake A J, Wilson C, Reid S D, Novak A, Hitchcock P B. *Chem. Commun.* 2003; 1682-1683.
25. a) Xie L Y, Dolphin D. *J. Chem Soc. Chem. Commun.* 1994; 1475-1476. b) Acholla F V, Takusagawa F, Mertes K B. *J. Am. Chem. Soc.* 1985; 107: 6902-6908. c) Reiter W A, Gerges A, Lee S, Deffo T, Clifford T, Danby A, Bowman-James K. *Coord. Chem. Rev.* 1998; 174: 343-359. d) Givaja G, Blake A J, Wilson C, Schröder M, Love J B. *Chem. Commun.* 2003; 2508-2509. e) Li R, Mulder T A. Beckmann U, Boyd P D W, Brooker S. *Inorg. Chim. Acta* 2004; 357: 3360-3368. f) Callaway W B, Veauthier J M, Sessler J L. *J. Porphyrins Phthalocyanines* 2004; 8: 1-25.

26. Reid S D, Blake A J, Köckenberger W. Wilson C, Love J B. *Dalton Trans.* 2003; 4387-4388.
27. Mizutani T, Ema T, Tomita T, Kuroda Y, Ogoshi H. *J. Am. Chem. Soc.* 1994; 116: 4240-4250.
28. Hammel D, Erk P, Schuler B, Heinze J, Müllen K. *Adv. Mater.* 1992; 4: 737-739.
29. Lee C H, Lindsey J S. *Tetrahedron* 1994; 50: 11427-11440.
30. Lee C H, Kim J Y. *Bull. Korean Chem. Soc.* 1996; 17: 215-217.
31. Boyle R W, Karunaratne V, Jasat A, Mar E K, Dolphin D. *Synlett* 1994; 939-940.
32. Oddo B, Cambieri F. *Gazz. Chim. Ital.* 1940; 70: 559-564.
33. Wang Q M, Bruce D W. *Synlett* 1995; 1267-1268.
34. Laha J K, Dhanalekshmi S, Taniguchi M, Ambroise A, Lindsey J S. *Org. Process Res. Dev.* 2003; 7: 799-812.
35. a) Vilsmeier A, Haack A. *Ber.* 1927; 60: 119-122. b) Kleinspehn G G, Briod A E. *J. Org. Chem.* 1961; 26: 1652-1654.
36. Tamaru Si, Yu L, Youngblood W J, Muthukumaran K, Taniguchi M, Lindsey J S. *J. Org. Chem.* 2004; 69: 765-777.
37. Chong R, Clezy P S, Liepa A J, Nichol A W. *Aust. J. Chem.* 1969; 22: 229-238.
38. Srinivasan N, Haney C A, Lindsey J S, Zhang W, Chait B T. *J. Porphyrins Phthalocyanines* 1999; 3: 283-291.
39. Littler B J, Ciringh Y, Lindsey J S. *J. Org. Chem.* 1999; 64: 2864-2872.
40. a) Adler A D, Longo F R, Shergalis W. *J. Am. Chem. Soc.* 1964; 86: 3145-3149. b) Adler A D, Longo F R, Finarelli J D, Goldmacher J, Assour J, Korsakoff L. *J. Org. Chem.* 1967; 32: 476.
41. a) Lindsey J S, MacCrum K A, Tyhonas J S, Chuang Y Y. *J. Org. Chem.* 1994; 59: 579-587. b) Ravikanth M, Achim C, Tyhonas J S, Münck E, Lindsey J S. *J. Porphyrins Phthalocyanines* 1997; 1: 385-394.
42. Lindsey J S. In *The Porphyrin Handbook*; Kadish K M, Smith K M, Guilard R. Eds.; Academic Press: San Diego, Calif., 2000; Vol. 1, 45-118.
43. Yu L, Muthukumaran K, Sazanovich I V, Kirmaier C, Hindin E, Diers J R, Boyle P D, Bocian D F, Holten D, Lindsey J S. *Inorg. Chem.* 2003; 42: 6629-6647.
44. Minkin V I, Korobov M S, Nivororozhkin L E, Kompan O E, Olekhnovich R Y, Borodkin G S, Struchkov Y T. *Mendeleev Commun.* 1993; 2-5.

The foregoing is illustrative of the present invention, and is not to be construed as limiting thereof. The invention is defined by the following claims, with equivalents of the claims to be included therein.

That which is claimed is:

1. A compound of Formula II:

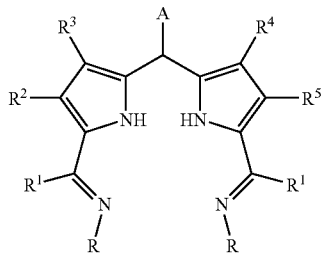

(II)

wherein:
R is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl;
$R^1$ is H, alkyl or aryl;
$R^2, R^3, R^4$, and $R^5$ are each independently selected from the group consisting of H, halo, loweralkoxy, and loweralkylthio; and
A is aryl.

2. The compound of claim 1, wherein A is an aromatic hydrophilic group, an aromatic surface attachment group, an aromatic cross-coupling group or an aromatic bioconjugatable group.

3. The compound of claim 2, wherein A is an aromatic alkene, alkyne, alcohol, thiol, selenyl, phosphono, carboxylic acid, formyl, halo or amine containing-group.

4. The compound of claim 1, wherein $R^2, R^3, R^4$, and $R^5$ are each independently selected from the group consisting of H and halo.

5. The compound of claim 1, wherein $R^2, R^3, R^4$, and $R^5$ are each H.

6. The compound of claim 1, wherein said compound has the formula:

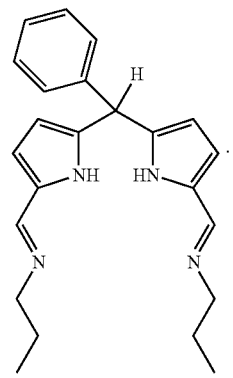

3a

7. A method of making a compound of Formula II:

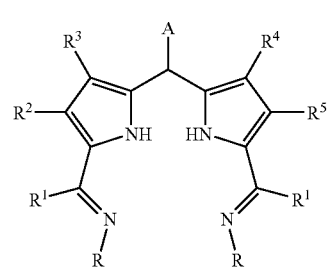

(II)

wherein:
R is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl;
$R^1$ is H, alkyl or aryl;
$R^2, R^3, R^4$, and $R^5$ are each independently selected from the group consisting of H, halo, loweralkoxy, and loweralkylthio; and A is aryl; said method comprising:
reacting a dipyrromethane of Formula IV:

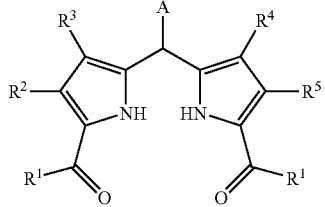
(IV)

wherein A, $R^1$, $R^2$, $^4$ and $R^5$ are as given above, with a compound of Formula V:

(V)

wherein R is as given above in an organic solvent to produce said compound of Formula II.

8. The method of claim 7, wherein A is an aromatic surface attachment group, an aromatic cross-coupling group or an aromatic bioconjugatable group.

9. The method of claim 8, wherein A is an aromatic alkene, alkyne, alcohol, thiol, selenyl, phosphono, carboxylic acid, formyl, halo or amine containing-group.

10. The method of claim 7, wherein $R^2$, $R^3$, $R^4$, and $R^5$ are each independently selected from the group consisting of H and halo.

11. The method of claim 7, wherein $R^2$, $R^3$, $R^4$, and $R^5$ are each H.

12. The method of claim 7, wherein said solvent is selected from the group consisting of methylene chloride, chloroform, tetrahydrofuran, nitromethane, toluene, acetonitrile, and mixtures thereof.

* * * * *

UNITED STATES PATENT AND TRADEMARK OFFICE
CERTIFICATE OF CORRECTION

PATENT NO. : 8,013,149 B2
APPLICATION NO. : 12/494711
DATED : September 6, 2011
INVENTOR(S) : Lindsey et al.

It is certified that error appears in the above-identified patent and that said Letters Patent is hereby corrected as shown below:

In the Patent:
Column 8, Formula (III), Line 25: Please correct

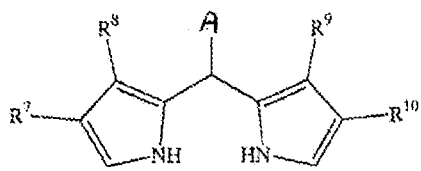

to read

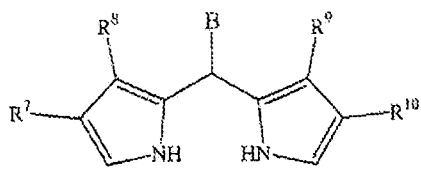

Columns 25-26, Table 1, Col. R, Entry 2: Please correct "b" to read -- c --

Columns 35-36, Table 5, Entry 1c, 4$^{th}$ column: Please correct "iS" to read -- 18 --

Column 47, Line 19: Please correct ", ∈=" to read -- ,ε= --

Column 53, Line 19: Please correct "$^8$H NMR" to read -- $^1$H NMR --

In the Claims:
Column 57, Claim 7, Line 15: Please correct "A, $R^1$, $R^2$, $^4$ and $R^5$"
to read -- A, $R^1$, $R^2$, $R^3$, $R^4$ and $R^5$ --

Signed and Sealed this
Thirty-first Day of January, 2012

David J. Kappos
*Director of the United States Patent and Trademark Office*